United States Patent [19]

Desai et al.

[11] Patent Number: 5,334,640

[45] Date of Patent: Aug. 2, 1994

[54] IONICALLY COVALENTLY CROSSLINKED AND CROSSLINKABLE BIOCOMPATIBLE ENCAPSULATION COMPOSITIONS AND METHODS

[75] Inventors: Neil P. Desai; Patrick Soon-Shiong; Paul A. Sandford; Roswitha E. Heintz, all of Los Angeles, Calif.

[73] Assignee: Clover Consolidated, Ltd., Lausanne, Switzerland

[21] Appl. No.: 866,038

[22] Filed: Apr. 8, 1992

[51] Int. Cl.$^5$ .......................... C08K 5/15; C08L 5/00; A61K 9/14; C12N 11/02
[52] U.S. Cl. ......................................... 524/56; 524/54; 524/28; 424/488; 424/499; 435/177; 435/178
[58] Field of Search ............................. 524/56, 54, 28; 424/488, 499; 435/177, 178

[56] References Cited

U.S. PATENT DOCUMENTS

| | | | |
|---|---|---|---|
| 4,177,038 | 12/1979 | Biebricher et al. | 435/178 |
| 4,352,883 | 10/1982 | Lim | 435/178 |
| 4,391,909 | 7/1983 | Lim . | |
| 4,409,331 | 10/1983 | Lim . | |
| 4,592,098 | 6/1986 | Aurameas et al. | 435/178 |
| 4,663,286 | 5/1987 | Tsang et al. . | |
| 4,744,933 | 5/1988 | Rha et al. . | |
| 4,749,620 | 6/1988 | Rha et al. . | |
| 4,791,061 | 12/1988 | Sumino | 435/178 |
| 4,798,786 | 1/1989 | Tice | 435/177 |
| 4,824,916 | 4/1989 | Kershner et al. | 525/420 |
| 5,041,292 | 8/1991 | Feijin | 424/488 |

FOREIGN PATENT DOCUMENTS

| | | | |
|---|---|---|---|
| WO91/07951 | 6/1991 | PCT Int'l Appl. . | |
| 9109119 | 6/1991 | PCT Int'l Appl. | 435/178 |
| WO91/11205 | 8/1991 | PCT Int'l Appl. . | |
| 2237574 | 5/1991 | United Kingdom | 524/28 |

OTHER PUBLICATIONS

Thesis re structural studies and the biosynthesis of aliginates by Gudmund Skjak-Braek, Trondheim, Norway, Jun. 1988, (pp. I-VI and 1-49).
Article *Applications of some Algal Polysaccharides in Biotechnology*, by Gudmund Skjak-Braek & Anita Martinsen, Norwegian Institute of Technology, Trondheim, Norway, 1991 John Wiley & Sons, Ltd. (pp. 219-257).
"Alteration of Immunological Properties of Bovine Serum Albumin by Covalent Attachment of Polyethylene Glycol" by Abraham Abuchowski, Theo van Es, Nicholas C. Palczuk and Frank F. Davis, Journal of Biological Chemistry, vol. 252, No. 11, Jun. 1977, pp. 3578-3581.
"Surface Topography Of Crosslinked Poly(ethylene oxide)/polysiloxane networks in the dry and hydrated states" by Elliott L. Chaikof, Edward W. Merrill, Sylvie L. Verdon, Lori L. Hayes, Raymond J. Connolly and Allan D. Callow, Polymer Communications, 1990, vol. 31, May, pp. 182-185.
"Synthesis of ionic conducting interpenetrating polymer networks" by Chiang, Bauer, Briber and Davis, Polymer Communications, 1987, vol. 28, Feb. pp. 34-36.
"Synthetic hyrogels: 7. High EWC semi-interpenetrating polymer networks based on cellulose esters and N-containing hydrophilic monomers" by Corkhill and Tighe, Polymer Communications, 1990, vol. 31, Aug. pp. 1526-1537.

(List continued on next page.)

*Primary Examiner*—Paul R. Michl
*Assistant Examiner*—Lavonda DeWitt
*Attorney, Agent, or Firm*—Pretty, Schroeder, Brueggemann & Clark

[57] ABSTRACT

Crosslinked biocompatible compositions comprising an ionically crosslinked component and a covalently crosslinked component for encapsulating biologics are disclosed. In accordance with the present invention, also disclosed are crosslinkable biocompatible mixtures comprising an ionically crosslinkable component and a covalently crosslinkable component. Methods for encapsulating biologics with the crosslinked and crosslinkable biocompatible compositions are provided. Also, retrievable macrocapsules for encapsulating microcapsules or biologics are disclosed.

36 Claims, 8 Drawing Sheets

OTHER PUBLICATIONS

"Real-Time Kinetic Study of Laser-Induced Polymerization" by C. Decker and K. Moussa, 1989 American Chemical Society, vol. 22, No. 12, pp. 4455–4461.

"Solution technique to incorporate polyethylene oxide and other water-soluble polymers into surfaces of polymeric biomaterials" by Neil P. Desai and Jeffrey A. Hubbell, Biomaterials 1991, vol. 12, Mar. pp. 144–153.

"In situ polymerization of a microencapsulating medium round living cells" by B. Dupuy, H. Gin, C. Baquey, and D. Ducassou. Journal of Biomedical Materials Research, vol. 22, 1061–1070 (1988).

"Synthesis and Characterization of Some Covalent Dextran-Polyoxyethyleneglycol Derivatives" by Jean Marc Duval, Christine Delestre, Marie-Christiane Carré, Patrick Hubert and Edith Dellacherie, Carbohydrate Polymers, vol. 15, 1991, pp. 233–243.

"Application of Photo-Crosslinkable Resin to Immobilization Of An Enzyme" by Fukui and Tanaka, FEBS Letters, vol. 66, No. 2, Jul., 1976, pp. 179–182.

"Entrapment of Biocatalysts With Photo-Cross-Linkable Resin Prepolymers and Urethane Resin Prepolymers" by Fukui, Sonomoio, and Tanaka. Methods In Enzymology, vol. 135, 1987.

"Synthesis and Characterization of Poly(ethylene Glycol) Derivatives" by Harris, Struck, Case and Paley. Journal of Polymer Science: Polymer Chemistry Edition, vol. 22, 1984, pp. 341–352.

"Effects Of Visible Radiation On Cultured Cells" by Tiina I. Karu, Photochemistry and Photobiology, vol. 52, No. 6, pp. 1089–1098, 1990.

"Influence of Hydration Ability of Monomer on Immobilization of Microbial Cells by Radiation Polymerization" by Minoru Kumakura and Isao Kaetsu, Journal of Applied Polymer Science, vol. 28, 2167–2175 (1983).

"Synthesis and Polymerization of Mono- and Divinyl Ethers of Oligooxyethylenes", Journal of Polymer Science: Polymer Letters Edition, vol. 20, 473–479 (1982).

"Covalently cross-linked sodium alginate beads" by Storker T. Moe, Gudmund Skjak-Braek and Olav Smidsrod. Food Hydrocolloids, vol. 5, No. 1, pp. 119–123, 1991.

"Complex-Forming Poly(oxyethylene): Poly(acrylic acid) Interpenetrating Polymer Networks. 1. Preparation, Structure, and Viscoelastic Properties." Macromolecules, vol. 18, No. 8, Aug. 1985, pp. 1519–1524.

"Detergents Linked to Polysaccharides: Preparation and Effects on Membranes and Cells" by Josef Pitha, Karol Kociolek and Marc G. Caron, European Journal Biochemistry, vol. 94, 1979, pp. 11–18.

"Alginate as immobilization matric for cells" by Olav Smidsrod and Gudmund Skjak-Braek, Trends in Biotechnology, vol. 8, No. 3[74], Mar. 1990, pp. 71–78.

"Attachment Of Drugs To Polyethylene Glycols" by S. Zalipsky, C. Gilon and A. Zilkha. European Polymer Journal, vol. 19, No. 12, 1983, pp. 1177–1183.

"Prolonged Pancreas Preservation Using A Simplified UW Solution Containing Polyethylene Glycol" by Tianli Zheng, Robert P. Lanza, and Patrick Soon-Shiong, Transplantation, vol. 51, No. 1, Jan. 1991, pp. 63–66.

IONICALLY COVALENTLY CROSSLINKED AND CROSSLINKABLE BIOCOMPATIBLE ENCAPSULATION COMPOSITIONS AND METHODS

BACKGROUND OF THE INVENTION

The present invention relates to compositions and methods for encapsulating biologics such as biologically active materials or diagnostic markers. More specifically, the present invention relates to an ionically and covalently crosslinked biocompatible material which provides a non-cytotoxic, immunoprotective barrier for a biologic, including a xenotransplanted biologic. In another aspect, the present invention relates to a mixture of an ionically crosslinkable component and a covalently crosslinkable component, suitable for use in encapsulating a biologic. The present invention also relates to processes for encapsulating biologics with the crosslinked biocompatible material.

Many biocompatible materials such as lipids, polycations, and polysaccharides, such as hyaluronic acid, have been used to encapsulate materials such as living cells and tissue. For instance, the polysaccharide alginate has been used for the encapsulation, immunoisolation, and immobilization of cells. The combination of alginate with multivalent cations, such as calcium, can form mechanically stable, ionically crosslinked microencapsules. However, when used in a physiological environment, such as in the transplantation of microencapsulated islets or cells, the mechanical stability of the ionically crosslinked alginate microcapsules will erode since the extracellular concentration of monovalent cations exceeds the concentration of the divalent calcium cations, resulting in the exchange by diffusion of the monovalent and divalent cations.

Attempts to chemically modify alginate microcapsules or gels by utilizing covalent crosslinking rather than ionic crosslinking have been made in order to improve mechanical stability. However, the reagents and reaction conditions involved with these techniques often prove toxic and even fatal to the encapsulated materials. In order to further improve mechanical stability, covalently modified alginates have been photopolymerized to produce covalently crosslinked alginate gels. The rapid photopolymerization or photocrosslinking of the alginate avoids the exposure of the encapsulated materials to the toxic species that are present during the above-described processes.

It has also been found that implanted alginate gels having higher fractions of $\alpha$-L-guluronic acid (G blocks) are more biocompatible than those containing a larger fraction of $\beta$-D-mannuronic acid (M blocks), since they do not induce a cytokine response from monocytes. Alginates having a higher fraction of M blocks on the other hand, induce a cytokine response when implanted in a physiological environment. This M block induced cytokine response results in fibrous overgrowth of the implanted alginate encapsulation material, thereby restricting the supply of nutrients and preventing the encapsulated material from permeating the encapsulation barrier for delivery to the physiological environment.

Polylysine has been used as an additional layer with microcapsules using high G-block alginates in order to improve chemical and mechanical stability. Nevertheless, although high G block alginate-polylysine gels have been demonstrated to successfully reverse diabetes in spontaneous diabetic dogs when used to encapsulate transplanted islets of Langerhans, the long term function of these ionically crosslinked gels have been hampered by chemical and/or mechanical disruption of the alginate-polylysine membrane, thereby resulting in rejection and fibrous overgrowth.

Water-insoluble polymers, such as acrylate polymers or copolymers, and methacrylate polymers or copolymers, have been used in efforts to improve the stability of encapsulation materials. Photopolymerized polyacrylamides have also been in this regard. Likewise, however, these materials, or the organic solvents associated with them, often prove cytotoxic to the encapsulated living cells. Moreover, these water insoluble polymers tend to be bioincompatible in vivo in the long-term.

Crosslinked polyethylene glycol (PEG) gels have been used to immobilize enzymes and microbial cells. Polymerizable derivatives of PEG, such as PEG dimethacrylate, have been photocrosslinked using ultraviolet light in the presence of a suitable initiator to form a gel. This technique is desirable for the encapsulation of not only enzymes, but also for cells and organelles, due to the absence of heating, the avoidance of extreme pH values, and the absence of toxic chemicals in the photopolymerization process.

Polyethylene glycol is generally suitable as a biocompatible, protein repulsive, non-inflammatory, and nonimmunogenic modifier for drugs, proteins, enzymes, and the surfaces of implanted material. These characteristics of polyethylene glycol are attributable to its non-ionic character, its water solubility, the flexibility of its backbone, and its volume exclusion effect in solution or when immobilized at a surface. Further, surfaces modified with PEG have been found to be extremely non-thrombogenic, resistant to fibrous overgrowth in vivo, and resistant to bacterial adhesion. PEG bound to bovine serum albumin has been shown to have reduced immunogenicity and increased circulation times in a rabbit.

PEG has been covalently bound to poly-L-lysine (PLL) to enhance the biocompatibility of alginate-PLL (PLL) microcapsules for encapsulation of cells. PEG has also been covalently bound to polysaccharides such as alginates in order to make them soluble in organic media. However, this material requires the additional steps necessary to chemically modify the alginate before it can be crosslinked.

Polyethylene glycol has also been utilized as a component of interpenetrating polymer networks (or IPNs), which are a combination of two or more different polymer systems, at least one of which is synthesized or crosslinked individually in the presence of the other. In particular, polyethylene glycol has been used as a component in IPNs with several polymers and monomers such as N-acryloylpyrrolidine, polysiloxane, epoxy resins, and poly acrylic acid. Nevertheless, the IPNs known in the art have not utilized alginates as one of the crosslinked components, nor are IPNs known in which one of the components is ionically crosslinked.

Although many of the polyethylene glycol gels known in the art elicit a very low fibrotic response in physiological environments, such gels often require an essential emulsion or co-extrusion step with an oil or water immiscible phase for the formation of droplets or microcapsules. This may result in some toxicity due to the possibility that some of the oil phase may be carried over into the implanted host.

Accordingly, there exists a definite need for gel or encapsulation materials which are not unstable under physiological conditions. There also exists a need for very mild and gentle methods for encapsulating biologics, especially for encapsulating living cells or tissues in an aqueous environment, whereby such methods allow a subsequent or simultaneous covalent crosslinking for chemical and mechanical stability without the necessity of a potentially toxic oil phase. Further, there exists a need for biocompatible encapsulation or microencapsulation materials which are mechanically and chemically stable in physiological environments. There also exists the need for such materials which provide immunoprotectivity of the encapsulated biologics. Additionally, there exists a need for biocompatible encapsulation materials which allow for the controlled release of an encapsulated biologic.

SUMMARY OF THE INVENTION

In accordance with the present invention, there are provided compositions and processes for encapsulating biologics, such as biologically active components and diagnostic markers. More specifically, the compositions of the present invention comprise a crosslinked biocompatible material having at least one ionically crosslinked component and at least one covalently crosslinked component. The crosslinked biocompatible materials are formed from mixtures having at least one ionically crosslinkable component and at least one covalently crosslinkable component.

The combination of an ionically crosslinked component and a covalently crosslinked component provides a non-cytotoxic, immunoprotective gel that can be used to entrap or encapsulate a biologic in a tightly crosslinked network, while preventing the diffusion of the ionically crosslinked component out of the crosslinked gel even in the presence of monovalent ions or ion chelators. The covalently crosslinked component further provides mechanical and chemical stability to the encapsulation material or gel. The ionically crosslinked component provides a matrix or pre-formed gel which facilitates the rapid covalent crosslinking of the covalently crosslinkable component without the necessity of an immiscible, potentially toxic oil phase required for the formation of gelled droplets or capsules. These dually crosslinked materials provide the required properties for immunoprotectivity of the encapsulated biologics (including xenotransplanted biologics) by preventing the migration of molecules through the material which are potentially harmful to the biologics. Furthermore, the biocompatible materials or compositions of the present invention provide for the controlled release of biologics, or components thereof, into the physiological environment for therapeutic purposes, such as drug delivery.

The present invention also is embodied in a crosslinkable biocompatible mixture suitable for encapsulating a biologic, such as biologically active materials or diagnostic markers, once it is properly crosslinked. The crosslinkable biocompatible mixture is comprised of an ionically crosslinkable component and a covalently crosslinkable component having at least one polymerizable functional group subject to free radical polymerization.

The present invention further relates to processes for encapsulating a biologic comprising coating the biologic with a composition having a covalently crosslinked component and an ionically crosslinked component.

In yet a further aspect of the invention, a retrievable encapsulation material is provided which is comprised of a macrocapsule of the crosslinked biocompatible material of the present invention for encapsulating free cells or other microcapsules.

Other features and advantages of the present invention will become apparent from the following detailed description, taken in conjunction with the accompanying drawings and examples, which illustrate the principles of the invention.

DETAILED DESCRIPTION OF THE PREFERRED EMBODIMENT

Figure 1:
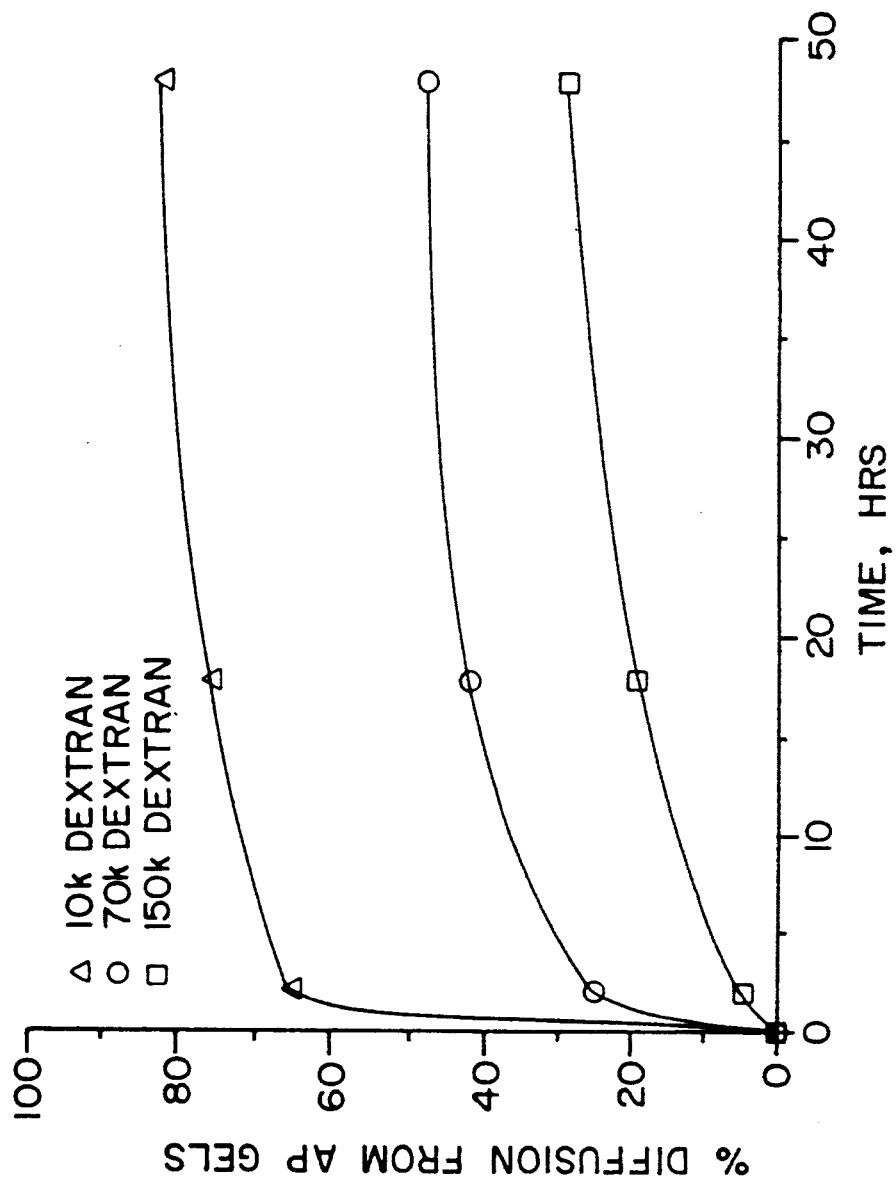
FIG. 1 is a graph showing the permeability of an alginate/PEG-DA (AP) 10K crosslinked encapsulation gel to different molecular weight dextrans.

In accordance with the present invention there is provided a crosslinkable biocompatible mixture for encapsulating biologics, such as biologically active materials or diagnostic markers. The crosslinkable biocompatible mixture is comprised of an ionically crosslinkable component and a covalently crosslinkable component. The ionically crosslinkable component is selected from a polysaccharide, a polyanion, or a polycation. The covalently crosslinkable component is selected from a polyalkylene oxide having at least one functional group capable of undergoing free radical polymerization.

The present invention also relates to crosslinked biocompatible materials having at least one ionically crosslinked component and at least one covalently crosslinked component. The crosslinked biocompatible materials are suitable for encapsulating biologically active materials, such as living cells, hormones, enzymes, tissues, drugs or pharmaceuticals, or diagnostic markers such as imaging contrast media, radio contrast media and the like.

Ionically crosslinkable polysaccharides suitable for the present invention include, but are not limited to, alginate and natural ionic polysaccharides such as chitosan, gellan gum, xanthan gum, hyaluronic acid, heparin, pectin and carageenan. Examples of ionically crosslinkable polyanions suitable for use in the practice of the present invention include, but are not limited to, polyacrylic acid and polymethacrylic acid. Ionically crosslinkable polycations such as polyethylene imine and polylysine are also suitable for use in the present invention.

In a preferred embodiment of the present invention, the polysaccharide alginate serves as the ionically crosslinkable component. (Alginate as used herein refers to salts of alginic acid.) Preferably, the alginate has a high fraction of $\alpha$-L-guluronic acid (G blocks) to prevent the inducement of a cytokine response from monocytes. More particularly, alginates having at least 60 percent, and preferably 70 percent or greater, $\alpha$-L-guluronic acid blocks are used in accordance with the present invention. Alginates having higher fractions of $\alpha$-L-guluronic acid or G blocks are more biocompatible than those containing a larger fraction of $\beta$-D-mannuronic acid or M blocks since high M block alginates have been found to induce fibrotic overgrowth.

Alginate in a concentration range of about 0.1% to 5% w/v is generally suitable when used as the ionically crosslinkable component in the biocompatible mixture of the present invention. Preferably, the alginate is provided in a concentration range of 1.5–2.0% w/v when used in a mixture containing particular concentrations of polyethylene glycol diacrylate (as discussed below) as the covalently crosslinkable component. It should be appreciated, however, that varying amounts or concentration ranges of alginates in the final mixture may be utilized in order to carry out the invention.

The ionically crosslinkable component is ionically crosslinked by the addition to the bicompatible encapsulation mixture of multivalent cations, such as calcium, zinc, barium, strontium, aluminum, iron, manganese, nickel, cobalt, copper, cadmium, lead, or mixtures of any 2 or more thereof. Calcium, barium, and strontium are preferable, with calcium being the most preferred for ionically crosslinking the ionically crosslinkable component of the mixture.

A polyalkylene oxide having at least one functional group capable of undergoing free radical polymerization is suitable as the covalently crosslinkable component of the present invention. An example of a suitable polyalkylene oxide is polyethylene glycol which is modified with at least one acrylate group to render it polymerizable. The polyethylene glycol acrylate, such as polyethylene diacrylate, or (PEG-DA), is capable of undergoing free radical polymerization. A wide variety of functional groups such as acrylate groups, vinyl groups, methacrylate groups, and the like can also be used to modify the polyethylene glycol to render it polymerizable.

Other suitable methods, however, may be utilized to modify PEG so that it is crosslinkable. For example, several methods may be utilized to prepare a modified PEG that is crosslinkable or polymerizable by introducing unsaturation at the ends of the PEG chain. A preferred way to modify polyethylene glycol is to treat it with acryloyl halide, such as acryloyl chloride. An esterification reaction between PEG and acrylic acid (or a higher homologue or derivative thereof) may be carried out in an organic solvent such as toluene in order to render the PEG polymerizable. A small amount of acid such as p-toluene sulfonic acid may be used to catalyze the reaction. Excess of one of the reactants, such as the acrylic acid, will drive this equilibrium reaction towards completion. The reaction mixture is refluxed for several hours. Since water is formed as a product of the reaction, the water may be continuously withdrawn by distillation of the azeotrope formed with toluene in order to drive the equilibrium towards the products. Standard purification schemes may be utilized.

Methacrylic acid, alkyl methacrylates or methacryloyl halides may be reacted in a similar fashion with PEG to obtain a crosslinkable derivative, as described by Fukui, S. and Tanaka, A., 1976; FEBS. Letters 66:179. Alternatively, PEG alkoxide may be reacted with acetylene gas to produce the vinyl ethers of PEG in order to produce a crosslinkable PEG derivative, as set forth in Mathias, L. J., Canterberry, J. B., and South, M., 1982; J. Polym. Sci., Polym. Lett. Ed. 20:473. PEG may be reacted with methacrylic anhydride to obtain PEG dimethacrylate.

A reaction between PEG and allyl chloride in a dry solvent, catalyzed by small amounts of stannic chloride, will also result in a crosslinkable PEG. It shall be appreciated by those of skill in the art that several other known techniques may be utilized to obtain polymerizable PEG derivatives.

Polyethylene glycols or PEGs having a wide range of molecular weights can be modified for use in accordance with the present invention. For example, PEGs having molecular weights from 200 to 500,000 could be modified as described above to render them polymerizable. PEGs in an intermediate range of about 1,000–35,000 are particularly preferred. In accordance with a most preferred embodiment, PEG having a molecular weight in the range of about 3,000–10,000 is modified with acrylate using acryloyl chloride for use in the present invention.

The modified PEG derivatives are crosslinked by free radical polymerization, preferably initiated by irradiation of the mixture with electromagnetic radiation, such as visible light, ultraviolet radiation, or lasers. In order to covalently photocrosslink the PEG-DA, a free radical initiator is added which could be a combination of a photoinitiator, such as ethyl eosin, a cocatalyst, such as triethanolamine, and optionally a comonomer, such as 1-vinyl 2-pyrrolidinone. It should be appreciated, however, that other photoinitiators, cocatalysts, and comonomers may be used to photocrosslink the PEG-DA. For example, if the PEG-DA is photocrosslinked using ultraviolet (UV) light rather than visible light, UV suitable photoinitiators include 2,2-dimethoxy-2-phenyl acetophenone, benzoin ethyl ether, 2,2-dimethyl phenoxyacetophenone, benzophenones and ionic derivatives thereof (for water solubility), benzils and ionic derivatives thereof, and thioxanthones and ionic derivatives thereof. Visible light photoinitiators such as, ethyl eosin, erythrosin, rose bengal, thionine, methylene blue, riboflavin, and the like, are also suitable. Other suitable cocatalysts include triethanolamine, methyl diethanolamine, triethylamine, arginine, and the like. It should be appreciated that the amount and type of comonomer used, if desired, may vary.

In accordance with the present invention, it has been found that a range of composition ratios of the ionically crosslinkable component to the covalently crosslinkable component in the mixture are effective for the formation of a stable, crosslinked biocompatible encapsulation material or gel. A range of concentrations for PEG-DA of particular molecular weight(s), and the composition ratio between alginate and PEG-DA in the mixture suitable for the formation of a stable, crosslinked biocompatible encapsulation gel can be determined in accordance with the present invention. As set forth immediately below and as discussed more specifically in the examples, the following concentrations of PEG-DA of particular molecular weights and the accompanying composition ratios (alginate to PEG-DA) have been found to be effective for forming a stable, ionically and covalently crosslinked encapsulation gel.

| Molecular Weight of PEG-DA | Concentration range of PEG-DA suitable for stable crosslinking properties when added to 1.8% alginate solution | Range of ratios (alginate:PEG-DA) acceptable for stable ionic and covalent crosslinking |
| --- | --- | --- |
| 1000 | 14–17% | 1:9.5–11.5 |
| 3400 | 9–12% | 1:5.5–1:7.5 |
| 10000 | 4–8% | 1:2.5–1:5.0 |
| 20000 | 4–8% | 1:3.0–1:5.0 |
| 35000 | 5–9% | 1:3.0–1:5.0 |
| 20M | 5–7% | 1:3.0–1:4.5 |

Further in accordance with the present invention, by using a covalently crosslinkable component of a particular molecular weight or a combination of molecular weights, it is possible to tailor the permeability or molecular weight cutoff (MWCO) of the mixture as may be required to achieve immunoprotectivity of the biologics in a physiological environment once the mixture has been crosslinked. Also, in this respect, it is possible to tailor a crosslinkable biocompatible mixture having a porosity effective for the controlled release of at least a portion of encapsulated biologics or any material produced or secreted by the biologics once the mixture has been crosslinked. Knowing the molecular dimensions of drugs, enzymes or the like that have therapeutic use, an encapsulation gel of the present invention could be synthesized that would release the encapsulated biologic at a desired rate. Examples of such implantation therapy could include the treatment of hemophilia by a sustained release of Factor VIII; the sustained release of human growth hormone; the sustained release of thyroid supplements or substitutes in patients that have undergone thyroidectomies; the sustained release of adrenal supplements or substitutes for replacement of adrenal function; the sustained release of estrogen for birth control and the like.

In yet another aspect of the present invention, the osmolarity and pH of the crosslinkable biocompatible encapsulation mixture are adjusted such that they are suitable for the biologics to be encapsulated. The osmolarity and pH of mixtures or solutions prepared for cell treatment should be as close to physiological conditions as possible. Physiological osmolarity is maintained at about 290 milliosmoles (mOsm)/kg and physiological pH is considered to be around 7.4. In the handling of islets of Langerhans, it has been determined that a slightly hyperosmolar (>290 mOsm/kg) environment is preferable, rather than a slightly hyposmolar (<290 mOsm/kg) environment.

Thus, the biocompatible mixture of the present invention can form an encapsulation material that may be ideally suited for biological or drug delivery systems. The Examples set forth below describe the use of alginate/polyethylene glycol diacrylate or AP gels in providing an immunoprotection barrier for islets of Langerhans for the treatment of autoimmune type I diabetes. Importantly, the compositions of the present invention can provide immunoprotection for islets of Langerhans, or other biologics, from highly discordant species when xenotransplanted in vivo, without any further need for immunosuppression. This technique thus opens the possibilities for treatment of a wide variety of disorders. Several disease states could be treated by encapsulation of the appropriate cell types. Among the potential cell types are dopamine secreting cells for treatment of Parkinsonism, nerve growth factor secreting cells for the treatment of Alzheimer's disease, hepatocytes for treatment of liver dysfunction, adrenaline/angiotension secreting cells for regulation of hypo/hypertension, parathyroid cells for replacing thyroid function, norepinephrine/metencephalic secreting cells for the control of pain, and erythropoietin secreting cells for use as artificial erythrocytes or red blood cells for oxygen transport.

Further, the treatment of several diseases requires the in vitro culture of biopsied cells to test the effects of drugs that offer potential treatments. Culturing these cells often takes several days, and often, weeks may pass before an effective drug is found that affects the cultured cells in the desired fashion. A quick substitute to this technique may be the encapsulation of these cells in accordance with the present invention and subsequent implantation in animals. These animals would then be treated or screened with a variety of drugs or chemotherapeutic agents, and a more realistic in vivo picture of the toxicity and efficacy of these drugs on the encapsulated cells may be obtained by examining these cells following retrieval from the animal. Such in vivo assessments would be difficult or impossible to perform without the benefits of immunoisolation afforded by this encapsulation technology.

In accordance with yet another aspect of the present invention, there is provided a process for encapsulating a biologic, comprising coating the biologic with a crosslinked biocompatible material having an ionically crosslinked component and a covalently crosslinked component. In an alternative embodiment, a biologic is encapsulated in a crosslinked network by ionically and covalently crosslinking a suspension containing a biologic, an ionically crosslinkable component, and a covalently crosslinkable component. In yet a further alternative embodiment, the process comprises suspending the biologic material in a mixture of an ionically crosslinkable component, and a covalently crosslinkable component; ionically crosslinking the ionically crosslinkable component; and covalently crosslinking the covalently crosslinkable component. The ionically crosslinkable component, such as alginate, is crosslinked by adding multivalent cations, such as calcium, to the mixture. The covalently crosslinkable component is crosslinked by initiating free radical polymerization, for example, by photocrosslinking or exposing the mixture to electromagnetic radiation, especially UV radiation or visible light, in the presence of a photoinitiating system as described.

The process of the present invention provides for a short time interval between the ionic crosslinking and the covalent crosslinking of the mixture. The longer the ionically crosslinked gel is formed prior to the covalent crosslinking of the covalently crosslinkable component, the greater the possibility exists that the components of the photoinitiating system will diffuse out of the gel and weaken the crosslinking process. Thus, by minimizing the time period between the covalent and ionic crosslinking of the mixture, a stable crosslinked encapsulation material is formed. Preferably, the time delay should be limited to less than about 5 minutes. However, it should be further recognized that encapsulation spheres or capsules of different sizes may require a much shorter or longer time frame between the crosslinking steps. In general, spheres of smaller size will have a larger diffusion surface compared to larger spheres containing the same total volume of material. Thus, the potential for loss of the components essential for photocrosslinking by diffusion is greater in smaller spheres and therefore the time interval between the ionic and photocrosslinking steps should be adequately minimized. The present invention also contemplates the simultaneous ionic and covalent crosslinking of the components of the mixture.

Microcapsules generated by conventional techniques, such as by coaxial flow with an air stream, are difficult to retrieve following peritoneal implantation due to their small size (on the order of a few hundred microns). A typical dosage in a dog involves the implantation of approximately 30 ml of capsules. Accordingly, a retrievable macrocapsule for containing microcapsules or free cells is provided in accordance with the present invention. A large number of individual microcapsules or free cells may be localized to a preferred region in the peritoneal cavity (or other implantation site) by embedding these microcapsules or cells in a macrocapsule. The macrocapsule preferably contains a therapeutic dosage of microcapsules or free cells. The macrocapsule is fabricated from the AP mixtures or the dually crosslinkable encapsulation mixtures of the present invention. For instance, the microcapsules may be suspended in an AP mixture that is in accordance with the present invention in order to obtain a gelled macrocapsule containing the microcapsules within it. Free cells may also be encapsulated in a macrocapsule in absence of microcapsules. Such a system of delivery is readily retrievable due to its physical dimensions. As examples, such retrievable macrocapsules could be in the shape of a sphere, a cylinder rod, a circular disk, a flat plate, a long thread, or the like.

The following examples are intended to illustrate and not limit the methods and applications of the present invention.

SYNTHESIS OF PHOTOCROSSLINKABLE POLYETHYLENE GLYCOLS

Example 1

Preparation of Polyethylene Glycol Diacrylate Using Acryloyl Chloride

Polyethylene glycol (PEG) (available from Aldrich Inc.) having a molecular weight of 10000 (abbreviated 10 k) was modified chemically to incorporate acrylate functionalities into the molecule in order to render it crosslinkable or polymerizable by free radical species.

PEG 10 k was dried thoroughly by heating it in a vacuum oven at 80° C. for 24 hours. Alternatively, the PEG could be dissolved in toluene and the solution distilled wherein any moisture present could be removed as an azeotrope with the toluene. 40 g of dry PEG were then dissolved in 200-250 ml of dry toluene (acetone, benzene, and other dry organic solvents may also be used). The solution was cooled in an ice bath before the addition of acryloyl chloride. A five-fold molar excess of acryloyl chloride was added (3.26 ml) and a base, triethylamine (5.54 ml), was added to remove HCl upon formation. The reaction could also be carried out in the absence of a base and the liberated HCl released in gaseous form.

The reaction was carried out in a round bottomed flask under argon with constant reflux for 24 hours. The reaction mixture was filtered to remove the insoluble triethylamine hydrochloride, while the filtrate was added to an excess of diethyl ether to precipitate the PEG diacrylate (PEG-DA). The product was redissolved in toluene and precipitated twice with diethyl ether for further purification, and any remaining solvent removed in the vacuum oven. The yield was 35 g of PEG-DA. Other purification schemes such as dialysis of a PEG-water solution against deionized water followed by freeze drying are also acceptable.

PHOTOCROSSLINKING OF PEG DERIVATIVES

Example 2

Visible Light Photocrosslinking to Produce PEG Gels

PEG derivatives prepared as described in Example 1 were dissolved in aqueous bicarbonate buffered saline at pH 7.4 (or other buffers) and a concentration of 1–40%. A photoinitiator, ethyl eosin ($0.10^{-7}$M to $10^{-4}$M), a cocatalyst, triethanolamine ($10^{-4}$M to $10^{-1}$M), and a comonomer, 1-vinyl 2-pyrrolidinone (0.001 to 1.0% of total vol., but not essential) were added to the solution which was protected from light until the photocrosslinking or photopolymerization process.

A small quantity of the prepared solution was taken in a test tube and exposed to visible radiation either from an argon ion laser at a wavelength of 514 nm at powers between 10 mW to 2 W, or a 100 watt mercury arc lamp which has a fairly strong emission around 500–550 nm. The gelling time was noted and found to be extremely rapid with the laser (on the order of milliseconds) and fairly rapid with the mercury lamp (on the order of seconds), and varied with the concentrations of polymer, initiator, cocatalyst, and comonomers in the system.

Example 3

UV Light Photopolymerization or Photocrosslinking to Produce PEG Gels

A different initiating system from the one described above was used to produce PEG gels. A ultraviolet (UV) photoinitiator, 2,2-dimethoxy-2-phenyl acetophenone, was added to a solution of polymerizable PEG in aqueous buffer at a concentration of 1000–1500 ppm. A small amount of dimethyl sulfoxide (DMSO) could be added to enhance the solubility of the photoinitiator. This solution was exposed to long wave length UV radiation from a 100 watt UV lamp. The time required for gelation was of the order of seconds and was a function of the concentration of initiator and the addition of a polymerizable comonomer such as vinyl pyrrolidinone (0.001 to 1.0%). A UV laser may also be used for the photopolymerization of the PEG.

HIGH G BLOCK ALGINATES

Example 4

Alginate can be prepared according to methods well known in the art. For example, alginate can be commercially obtained from numerous outlets including Sigma (St. Louis, Mo.) and Protan A/S (Drammen, Norway).

Poly G alginate may be obtained from Protan (Norway or Seattle), or may be obtained by isolation of the material from natural sources or by chemical conversion by methods well known in the art. Some alginate is relatively high in M block residues and must be converted to low M blocks for use in accordance with the preferred aspect of this invention. An example of a procedure which can be used for reducing the level of M blocks in alginate follows.

Commercial alginate from the algae *Laminaria hyperborea* containing 64% guluronic acid residues was obtained from Protan A/S, Drammen, Norway (Protan batch number BL 5417368). Lipopolysaccharide (LPS) contamination in the alginate was removed by the method described by Karplus et al. [("A new method for reduction of endotoxin contamination from protein solutions"; *J. Immunol. Methods,* (1987) 105:211)] using a combination of (1) Polymyxin-B-sepharose 4B (PB-seph 4B) (Pharmacia, Uppsala, Sweden) affinity binding and (2) endotoxin-protein dissociation with the dialyzable surfactant octyl-$\beta$-D-glucopyranoside (OBDG, Sigma, St. Louis, Mo., USA).

Briefly, 1% (w/v) OBDG was added to 1% (w/v) of the alginate solution (dissolved in elution buffer consisting of $NaHCO_3$ pH 8.5), and mixed for 30 minutes at room temperature. Equal volumes of the PB-Seph 4B-gel and OBDG/alginate solution were mixed and transferred to a dialysis bag (MW 12-14000). The bag was then placed in a container with phosphate buffered saline (PBS) and dialyzed for 48 hours at room temperature. Subsequently, the PB-Seph 4B-gel was removed by centrifugation at 2750 r.p.m., for 10 minutes at 4° C. 0.2% NaCl (w/v) was added to the alginate solution and the alginate was precipitated with 96% ethanol. The alginate was then washed twice with 96% ethanol and finally once with 96% ethanol and once with diethylether before it was dried. This alginate is referred to herein as poly-G alginate or G-block alginate or high G block alginate. Alginate fragments containing more than 85% G units, and a degree of polymerization of 40 G blocks (or $DP_n = 40$), can also be prepared from *Laminaria digitata*.

MIXTURES OF ALGINATE AND PEG-DIACRYLATE FOR SIMULTANEOUS OR SEQUENTIALLY CROSSLINKED ENCAPSULATION GELS OR INTERPENETRATING POLYMER NETWORKS

Example 5

Determination of Concentration Ranges of Mixtures of Alginate and PEG-Diacrylate Required for the Formation of Stable Crosslinked Encapsulation Gels A solution of sodium alginate in saline was prepared at a final concentration of 1.8% (w/v). PEG-DA 10 k prepared as described in Example 1 was added to this solution at final concentrations ranging from 1% to 30% (w/v) and these solutions tested for ionic crosslinkability of the alginate followed by the covalent photocrosslinkability of the PEG-DA. Since a dual property solution was desired, namely one possessing the unique qualities of ionic crosslinkability as well as chemical or covalent crosslinkability, these solutions were tested to satisfy both requirements.

Ionic crosslinking was tested by dropping a small quantity of the solution in a beaker containing a 0.4% calcium chloride solution. The criterion for passing this test was the instantaneous formation of a gelled mass upon contact of the alginate/PEG-DA mixture (abbreviated AP) with the calcium solution. Those solutions forming very soft gels or ones that did not rapidly form a gel were considered to fail this test. Similarly, the test for chemical or covalent crosslinking was conducted by addition of 5 $\mu$l/ml of a solution of ethyl eosin (consisting of 5 mg. of ethyl eosin in 1 ml. of 1-vinyl 2-pyrrolidinone), and 5 $\mu$l/ml of a solution of triethanolamine (TEA), 70% by volume in saline, to the AP solutions. The AP mixtures were then exposed to a 100 watt mercury lamp for 15 seconds following thorough mixing. If a consistent gel was not formed during this exposure, the AP solution was considered unstable and thus failed the test for chemical or covalent crosslinkability. These results are summarized in the following table.

| PEG-DA 10k concentration (w/v) % | Ionic Crosslinking 0.4% $CaCl_3$ | Photocrosslinking 15 sec exposure |
|---|---|---|
| 1 | ++ | − |
| 2 | ++ | − |
| 3 | ++ | − |
| 4 | ++ | + |
| 5 | + | + |
| 6 | + | + |
| 7 | + | ++ |
| 8 | − | ++ |
| 9 | −− | ++ |
| 10 | −− | ++ |
| 15 | −− | ++ |
| 20 | −− | ++ |
| 30 | −− | ++ |

Whereby, "++" equals very consistent gel;
"+" equals moderately consistent gel;
"−" equals poor gel quality;
"−−" equals no gelling.

The AP mixtures passing both the above criteria (i.e., those having a net positive score, namely the AP mixtures containing 1–8% of PEG-DA) were further tested as follows. Droplets of these AP mixtures containing ethyl eosin and triethanolamine at concentrations mentioned above were formed in a calcium solution. The droplets were exposed to a 100 Watt mercury (Hg) lamp while suspended in the calcium solution. The bleaching of the ethyl eosin (i.e., red to colorless) was observed over 30 seconds. Photobleaching of the dye is an indication of polymerization. Following this exposure, the now dually crosslinked droplets were tested for stability in a solution of sodium citrate (1.0M, a calcium chelator). A dissolution or fragmentation of the dually crosslinked gels under these rigorous conditions was considered as a failure of adequate covalent photocrosslinking. A range of concentrations of AP mixtures was arrived at that formed a stable gel in accordance with the sodium citrate test. The concentrations within this range were considered for further use in biological applications. The following table summarizes the selection criteria for the above described tests.

| PEG-DA 10k concentration (w/v) % | Bleaching after 30 second exposure | Exposure to 1M Sodium citrate, 15 minutes |
|---|---|---|
| 1 | yes | −− |
| 2 | yes | −− |
| 3 | yes | − |
| 4 | yes | + |
| 5 | yes | ++ |
| 6 | yes | ++ |
| 7 | yes | ++ |

-continued

| PEG-DA 10k concentration (w/v) % | Bleaching after 30 second exposure | Exposure to 1M Sodium citrate, 15 minutes |
|---|---|---|
| 8 | yes | + + |

Whereby, "+ +" equals no dissolution;
"+" equals mild dissolution;
"−" equals fragmentation;
"− −" equals total dissolution.

From the above tables, a range of concentrations (4–8%) was selected as adequate for forming dually or ionically and covalently crosslinked AP gels. It was evident that an interference in ionic crosslinking was observed at concentrations of PEG-DA 10 k above 8%.

Similar tests as outlined above were performed with PEG diacrylates synthesized from PEG of molecular weights ranging from 1000 to 35000 g/mol. For each molecular weight of PEG-DA, a suitable range of concentrations of PEG-DA in the AP mixture was found which both stable ionic and covalent crosslinking were possible. It is also possible to use mixtures of PEGs of different molecular weights in different proportions to achieve dual crosslinking capabilities. This latter method can be useful in tailoring the molecular weight cutoff (MWCO) of a crosslinked alginate/PEG-DA gel. The diffusion characteristics and MWCO of these gels is addressed in Example 7. Suitable concentration ranges of PEG-DA in AP mixtures (on a weight/final volume basis) showing stable dual crosslinking properties are summarized below.

| Molecular Weight of PEG-DA | Concentration range of PEG-DA suitable for stable dual crosslinking properties when added to 1.8% alginate solution |
|---|---|
| 1000 | 14–17% |
| 3400 | 9–12% |
| 10000 | 4–8% |
| 20000 | 4–8% |
| 35000 | 5–9% |
| 20M | 5–7% |

It is evident that the preparation of the above solutions by the addition of PEG-DA into a 1.8% solution of alginate resulted in the dilution of alginate in that solution and a concomitant drop in alginate concentration that was proportional to the amount of added PEG-DA. The final alginate concentration was however retained between 1.5–2.0%. To make the composition of the mixtures easily comprehensible, the amount of PEG-DA added was normalized to the amount of alginate present in the solution and expressed as a ratio. An acceptable range of ratios (alginate:PEG-DA) was determined for each molecular weight of PEG-DA tested. The results expressed in this fashion are tabulated below.

| Molecular Weight of PEG-DA | Range of ratios (alginate:PEG-DA) acceptable for stable dual crosslinking |
|---|---|
| 1000 | 1:9.5–1:11.5 |
| 3400 | 1:5.5–1:7.5 |
| 10000 | 1:2.5–1:5.0 |
| 20000 | 1:3.0–1:5.0 |
| 35000 | 1:3.0–1:5.0 |
| 20M | 1:3.0–1:4.5 |

Utilizing these ratios, a solution of alginate and PEG-DA can be made up with the final concentration of alginate in the solution preferably between 1.5% to 2% (weight/final volume), but not limited to this range. As an example, an ionic and covalent or dually crosslinkable mixture containing PEG-DA 10 k at the ratio of 1:3.5 is made using 1 g of alginate with 3.5 g of PEG-DA 10 k, and making up the mixture to an alginate final concentration of 1.7%, i.e. by making up the volume to 58.8 ml by addition of water (final concentration of alginate = $(1/58.8) \times 100 = 1.7\%$). The concentration of PEG-DA in the solution is then = $(3.5/58.8) \times 100 = 5.95\%$.

To test the effect of dilution with water on a particular acceptable AP mixture (as determined from the table above), the above described mixture (1:3.5 alginate:-PEG-DA 10 k) was prepared at three different final concentrations of alginate at 1.2%, 1.7%, and 2.1%. Droplets of these mixtures (containing photocatalysts) were formed in a calcium solution followed by exposure to light and a 1M sodium citrate solution. In each case, the droplets remained stable in citrate indicating that a dilution in the range of 1.2–2.1% alginate did not disrupt the dual gelling capability.

Example 6

Effect of Time Delay Between Ionic Crosslinking and Covalent Photocrosslinking on Stability of the Crosslinked Encapsulation Material or Gel An ionically gelled sphere of an AP mixture that has not as yet been covalently crosslinked is likely to lose its ability to covalently photocrosslink if there is a long time delay between the ionic and photocrosslinking steps. This loss in ability to photocrosslink is in all likelihood due to the diffusion of species that are active in the photocrosslinking process from the ionically gelled sphere into the surrounding solution. As the local concentrations of these species (for example, PEG-DA, ethyl eosin, triethanolamine, vinyl pyrrolidinone) within the gelled sphere decrease, its ability to form enough covalent crosslinks to retain stability upon exposure to a sodium citrate solution correspondingly decreases. Thus, the time delay between the two crosslinking steps is likely to be of prime importance in the formation of a stable, ionically and covalently crosslinked gel.

The effect of a time delay between the ionic and covalent photocrosslinking steps was tested with an AP mixture containing a 5% concentration of PEG-DA and a photoinitiating system (as described above). Gelled spheres (3–4 mm in diameter) were prepared in a 0.4% calcium chloride solution and then exposed to radiation from a Hg lamp (for 30 seconds) following a known time delay. The spheres were observed for bleaching (an indication of crosslinking or polymerization) and then transferred to a sodium citrate solution for 15 minutes. The integrity of the spheres was examined and conclusions were made regarding a maximum allowable time delay between the two crosslinking steps that would result in a stable dually crosslinked gel. The results are summarized in the table below.

| Time Delay between Ionic & Photo crosslinking | Bleaching after 30 sec exposure to Hg lamp | State of gel exposed to 1M sodium citrate, 15 minutes |
|---|---|---|
| 10 sec | yes | ++ |
| 30 sec | yes | ++ |
| 1 min | yes | ++ |
| 5 min | yes | ++ |
| 10 min | yes | − |
| 15 min | yes | − |

Whereby, "++" equals retains integrity;
"+" equals mild dissolution;
"−" equals loss in form;
"− −" equals fragmentation.

The above results clearly indicate the importance of limiting the time delay to preferably no more than about five minutes between the two crosslinking steps. Upon examination of these spheres in citrate after 24 hours, it was found that spheres subject to a 15 minute time delay were fragmented while the remainder maintained their states that were observed after 15 minute exposure to the sodium citrate solution. It of course should be recognized that for spheres of a different size or shape, the acceptable time delay can be readily determined, but it suffices to say that the time delay should be as small as possible.

ASSAYS FOR THE SUITABILITY OF DUALLY CROSSLINKABLE GELS IN BIOLOGICAL SYSTEMS

Example 7

Immunoprotective Effects of AP Encapsulation Gels as Determined by Diffusion of Suitable Labelled Macromolecules The diffusion of FITC (fluorscein isothiocyanate) labelled dextrans of known molecular weights through crosslinked AP gel beads was used to determine the diffusibility or molecular weight cutoff (MWCO) of the gel beads in order to elucidate their immunoprotective nature. AP solutions containing 6% PEG-DA 10 k and 1% FITC--dextrans having molecular weights 10000, 70000, and 150000 were prepared. Appropriate amounts of the photoinitiators were added to the solution and spherical beads were prepared by dropping a fixed volume (0.5 ml) of the solution into a 0.4% calcium chloride solution using a 1 ml syringe with a 20 gauge needle. About 35-45 beads were produced from 0.5 ml of the solution. Immediately following this step, the ionically gelled beads were covalently photocrosslinked by exposure to a Hg lamp for 30 seconds. The beads were then allowed to sit in the calcium solution for 10 minutes, following which they were washed three times in a Hanks balanced salt solution (obtained from Flow Laboratories, Inc., McLean, Va.) and incubated in 5 ml of this solution at 4° C. The absorbance of these solutions at 490 nm were measured periodically in a spectrophotometer and the amount of FITC-dextrans released from the beads was calculated from standard curves of absorbance versus concentrations prepared prior to the experiment. FIG. 1 shows the permeability of an alginate/PEG-DA 10 k dually crosslinked gel to different molecular weight dextrans.

Clearly, the permeability of the crosslinked encapsulation gel is a function of the molecular weight of the dextrans, with the 150 k dextran showing a significantly lower release than the lower molecular weight dextrans.

By using a higher concentration of the 10 k PEG-DA, or a lower molecular weight PEG-DA, or mixtures of PEG-DA of varying molecular weights, or a combination of PEG-DA with low molecular weight water soluble monomers (e.g. 1-vinyl-2-pyrrolidinone, hydroxyethyl methacrylate, or acrylamide, or the like), the permeability of the dually crosslinked gels may be tailored to particular specifications. An example of a desired specification would be a very low permeability to macromolecules having molecular weights greater than 150,000 daltons as may be required to achieve immunoprotectivity. As detailed herein, the dually crosslinked gels of the present invention also provide immunoprotection, without the need for further immunosuppression, for biologics from highly discordant species when xenotransplanted in vivo.

Example 8

Preparation of an AP Mixture for Islet Cell Encapsulation

AP mixtures or solutions were made up while carefully monitoring pH and osmolarity. An example of the preparation of an AP solution containing 10 k PEG-DA is outlined here. Similar steps are followed when different PEGs or other monomers are used in this mixture.

It was desired to prepare an AP solution containing PEG-DA 10 k at a final concentration of 6% (w/v) and sodium alginate at a final concentration of about 1.7% (w/v). A final volume of 200 ml was desired. The following components were mixed together: deionized water (186.4 ml), a 70% solution of triethanolamine in 0.9% saline (1 ml), a 5 mg/ml solution of ethyl eosin in vinyl pyrrolidinone (1 ml), and sodium chloride (0.8 g). The pH of this solution was adjusted to 7.2 by addition of 5N HCl. 12 g of PEG-DA 10 k and 3.4 g of sodium alginate were added and the solution stirred overnight in the dark. This solution was light sensitive and was therefore protected from light at all times. Following the dissolution of PEG and alginate, the osmolarity of this solution was adjusted to 290-350 mOsm/kg by addition of a small quantity of a saturated NaCl solution in deionized water. Verification of pH of the solution was found to be of critical importance since a high pH strongly affected islet function while a pH below 6.4-6.5 would render the mixture nonpolymerizable or noncrosslinkable when exposed to electromagnetic radiation or light because most of the triethanolamine would be present in the protoneted form and therefore unable to produce free radicals necessary for polymerization.

The solution was tested for ionic crosslinking as well as covalent photocrosslinking and was also subjected to the citrate test described earlier to verify its stability. The solution was then sterile filtered by pumping it through a 0.2 micron hollow fiber system. The sterile solution was stored in a refrigerator for later use.

Example 9

Encapsulation of Islets of Langerhans in AP Encapsulation Gels

Islets of Langerhans isolated from dogs, rats, pigs, or humans were obtained by techniques known in the art and maintained in culture. Prior to encapsulation, they were washed in saline and precipitated as a pellet by centrifugation. This pellet was resuspended in the AP mixture at a concentration of approximately 5000 islets/ml of AP mixture. This suspension was pumped through a coaxial flow jethead with concentric air flow to produce droplets of a desired size. Droplets produced by this technique were typically 200-700 microns in diameter. The droplets were collected in a beaker containing 0.4% calcium chloride solution where they instantly gelled by ionic crosslinking on contact with the solution. A calcium chloride solution of 0.1-2.0% can be used, but preferably a 0.4-0.8% solution is used. The transparent glass collection vessel was exposed to electromagnetic radiation (Hg lamp, 100 watt) with a bandpass green filter (transmission 500-580 nm) with a peak transmission around 550 nm. This wavelength range is coincidental with the absorption spectrum of ethyl eosin which functions as the dye or photoinitiator in the system. Ultraviolet and other wavelengths were screened out to prevent potential damage to the islets.

The ionically crosslinked droplets or capsules were simultaneously polymerized or photocrosslinked upon exposure to electromagnetic radiation, or light. This resulted in dually (i.e., ionic and covalent) crosslinked droplets or capsules containing islets. Exposure of these cells to light was limited to about five minutes although no evidence of deterioration or damage to islet function was observed at longer times. The capsules were thoroughly rinsed in saline and culture media and then put into culture.

Alternatively, large capsules (on the order of mm) could be prepared by injecting the solution through a syringe. Also, microcapsules prepared by conventional techniques could be further encapsulated in a 'macrocapsule' by this technique, the benefits of which are discussed below.

Example 10

In Vitro Tests of Islet Function Following Encapsulation with AP Mixtures

Static glucose stimulations (SGS) were performed on the encapsulated islets to assess islet function. Staining with dithizone or acridine orange/propidium iodide was done to assess viability. Briefly, the SGS technique involves stimulation of islets with a high level of glucose and measurement of the secreted insulin (by RIA) in response to the glucose level. The islets are first incubated for an hour in a basal level of glucose (typically 40-60 mg %) followed by incubation at a stimulatory level for an hour (300-400 mg %) and then back down to a basal level of glucose for an hour. An increase in the secreted insulin level above the basal secretion during the stimulation phase, followed by a return in secreted insulin to basal levels is a requisite for good islet function.

Two controls were used for this experiment. They were free islets and islets encapsulated in the conventional alginate/polylysine microcapsules (such as those disclosed in U.S. Pat. Nos. 4,352,883, 4,391,909, and 4,409,331.) The stimulation ratios (relative to initial basal insulin levels) for the free islets were 1.0:6.6:1.6, ratios for the alginate/polylysine encapsulated islets were 1.0:11.0:2.5, while levels for the AP encapsulated islets were 1.0:17.0:6.35. (The first number in the ratio refers to the normalized basal insulin level, the second refers to the insulin level in response to the glucose challenge, and the third to the basal level after the glucose challenge.) These results indicated adequate islet function and, along with viability staining, confirmed that there was no apparent damage to islet function as a result of the polymerization process or presence of other monomers and catalysts. It indicated, in fact, that the treatment of islets with the AP mixtures resulted in a better stimulation of islets in terms with insulin output.

Example 11

In Vitro Tests of Islet Function by Perifusion Following Encapsulation of Islets with AP Mixtures, Effect of Capsule Size on Kinetics of Insulin Release Canine islets in conventional alginate-polylysine microcapsules as described in U.S. Pat. No. 4,663,286) as well as islets encapsulated by the AP mixtures of the present invention (300-800 microns diameter) were tested for insulin secretion in a perifusion apparatus. Perifusion involves the testing of the islet response to a stimulatory level of glucose in a flowing system rather than a static system as described above. It is therefore possible to obtain the kinetics of insulin release by using this technique. Culture medium containing an appropriate amount of glucose is perfused through the system that has a chamber containing encapsulated islets and the perfused medium is collected periodically in a fraction collector and assayed for released insulin by RIA. In this particular test, a basal level of glucose (40 mg %, or 40 mg of glucose/100 ml of medium) was maintained for the first 60 minutes followed by a stimulatory level of glucose (300 mg %) for 30 minutes and a return to basal levels of glucose (40 mg %) for the remainder of the experiment.

Figure 2:
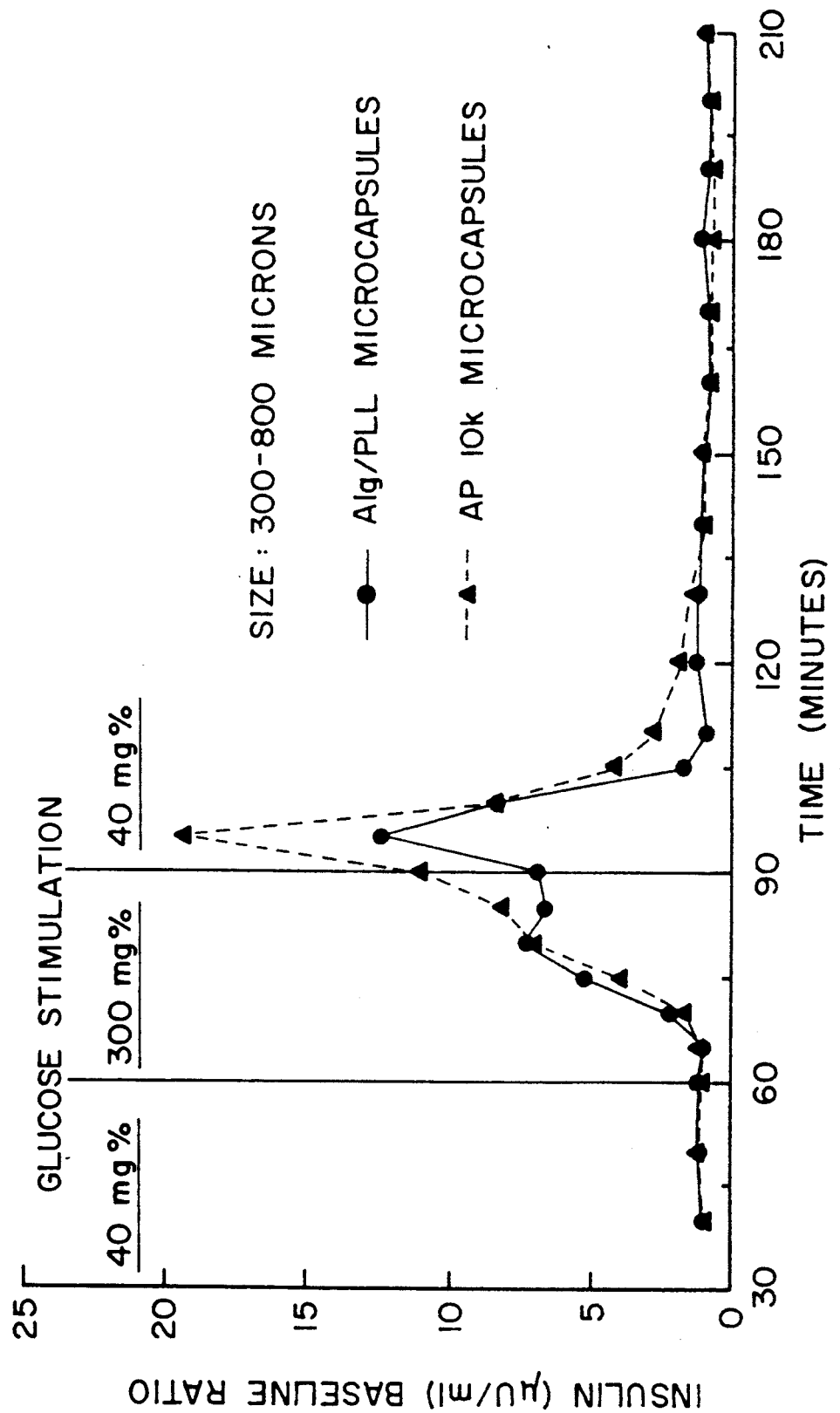
FIG. 2 is a graph comparing perifusion of canine islets in alginate/poly-L-lysine microcapsules and the AP 10K microcapsules of the present invention.

The results as illustrated in FIG. 2 show a distinct increase in insulin output measured relative to basal levels of insulin (at 40 mg % glucose) secreted by the islets when the chamber is perfused with medium containing 300 mg %. There is a lag phase of typically about 10 minutes before the islets start secreting an increased amount of insulin in response to the stimulatory level of glucose. About 15 minutes after the stimulation is ended, the insulin output from the islets falls back to basal levels of secretion. Clearly there is no difference in the kinetics of the response (or rapidity of the response) to increased glucose levels between the conventionally encapsulated islets (alg/PLL capsule) and the AP encapsulated islets. The AP encapsulated islets however show a greater stimulation in terms of insulin output than the alginate/PLL encapsulated islets.

Figure 3:
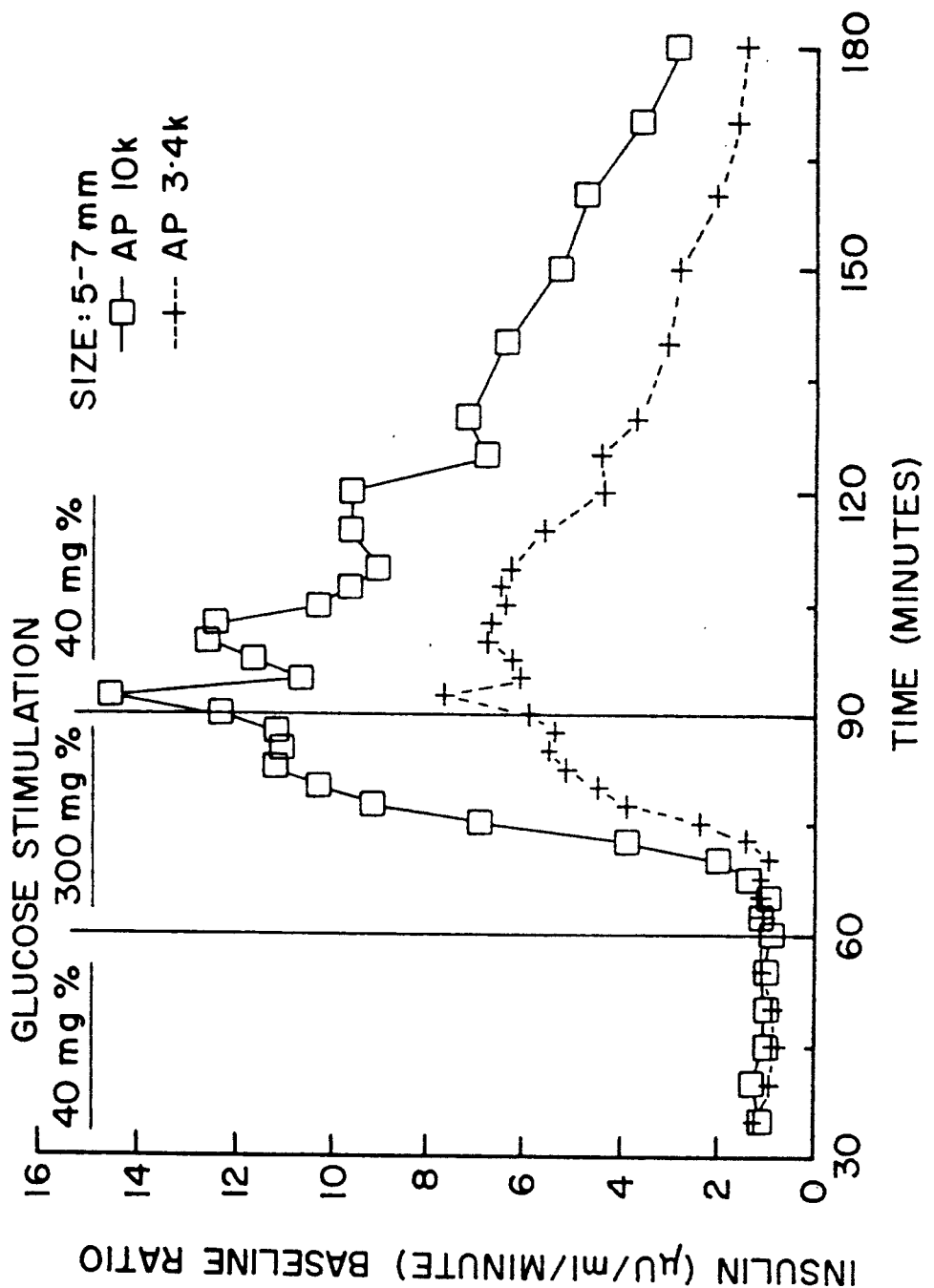
FIG. 3 is a graph comparing perifusion of canine islets in different molecular weight AP macrocapsules of the present invention.

To assess the effect of size of microcapsules on the kinetics of insulin release, larger microcapsules or "macrocapsules" were prepared containing canine islets. These macrocapsules (typically 5-7 mm diameter) were prepared simply by extruding a suspension of islets in the AP solution through a syringe and forming droplets in a calcium solution followed by photocrosslinking. AP solutions containing two different molecular weights of PEG-DA were prepared. They were AP 10 k (with PEG-DA 10000 MW) and AP 3.4 k (with PEG-DA 3400 MW). Macrocapsules of these materials containing canine islets were perifused to obtain the insulin release profiles as shown in FIG. 3. Islets encapsulated in the different AP solutions both showed a response to increased glucose within 10-15 minutes after the stimulus began. Thus there was no significant difference between the microcapsules and macrocapsules in terms of rapidity of insulin release following a stimulus of glucose. This was an important observation since it suggested that the size of the capsule may not be of importance in the kinetics of insulin response. On the other hand, the "downregulation" of insulin release seemed to occur much more slowly for the macroencapsulated islets providing a slow release system of insulin that may have advantages over the rapid downregulation seen in microencapsulated islets. This provides the potential advantage of a continuous low level baseline of insulin in vivo.

Thus, it was clear that the decreased porosity expected in case of the AP 3.4 k gel compared to the AP 10 k gel did not affect the diffusion of small molecules such as glucose and insulin through these gels although the diffusion of macromolecules may be affected.

Figure 4:
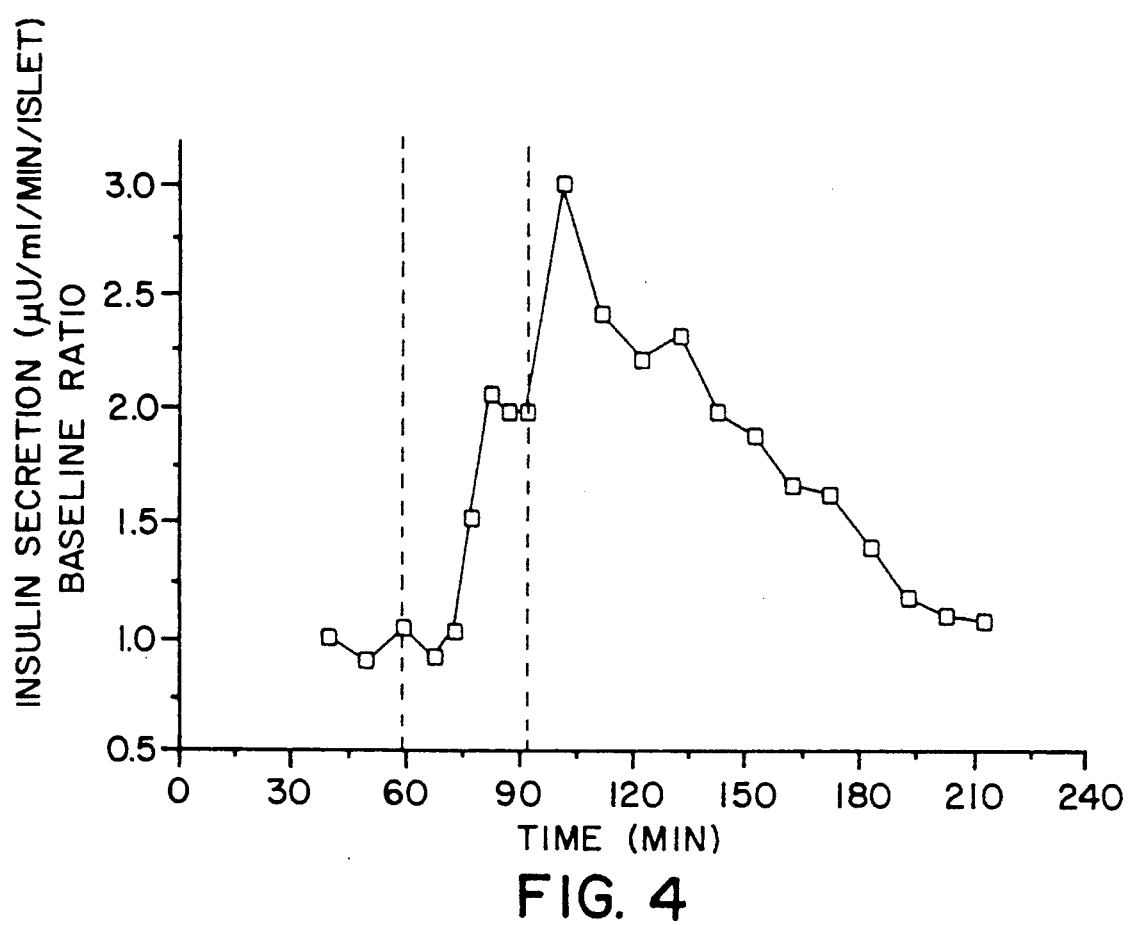
FIG. 4 is a graph showing insulin secretion response of canine islets in alginate-polylysine microcapsules further encapsulated in AP macrocapsules.

Canine islets in conventional alginate-polylysine microcapsules were also further encapsulated in AP macrocapsules. The results in FIG. 4 clearly show the initial basal level of secreted insulin followed by an insulin secretion response to the stimulatory level of glucose (for the time period between dashed lines) and a slow return to basal insulin secretion levels towards the end of the experiment.

It should be noted once again that the response to stimulus lags by about 10-15 minutes and this is comparable to the microcapsules and macrocapsules above. The downregulation is slower compared to the microcapsules as observed for the macrocapsules above. Nevertheless, the results are once again indicative of healthy functioning islets and the relatively innocuous encapsulation procedure.

Example 12

In Vivo Tests of Function of AP Encapsulated Islets in a Xenotransplant Model Followed by Retrieval of Functioning Implants Islets were encapsulated in a microcapsule of the AP 10 k solution. The procedure involved suspension of the islets in a AP solution and formation of tiny droplets (300-800 microns) by injection of the suspension through a coaxial flow jethead (with an external air flow) and subsequent photopolymerization by exposure to green light from a Hg lamp. The droplets were rinsed thoroughly in saline and culture media. They were cultured for three days before transplantation into the peritoneal cavities of streptozotocin (STZ) induced diabetic rats. The rats were kept in metabolic cages and their blood glucose, urine volume, and body weight were measured routinely.

Figure 5:
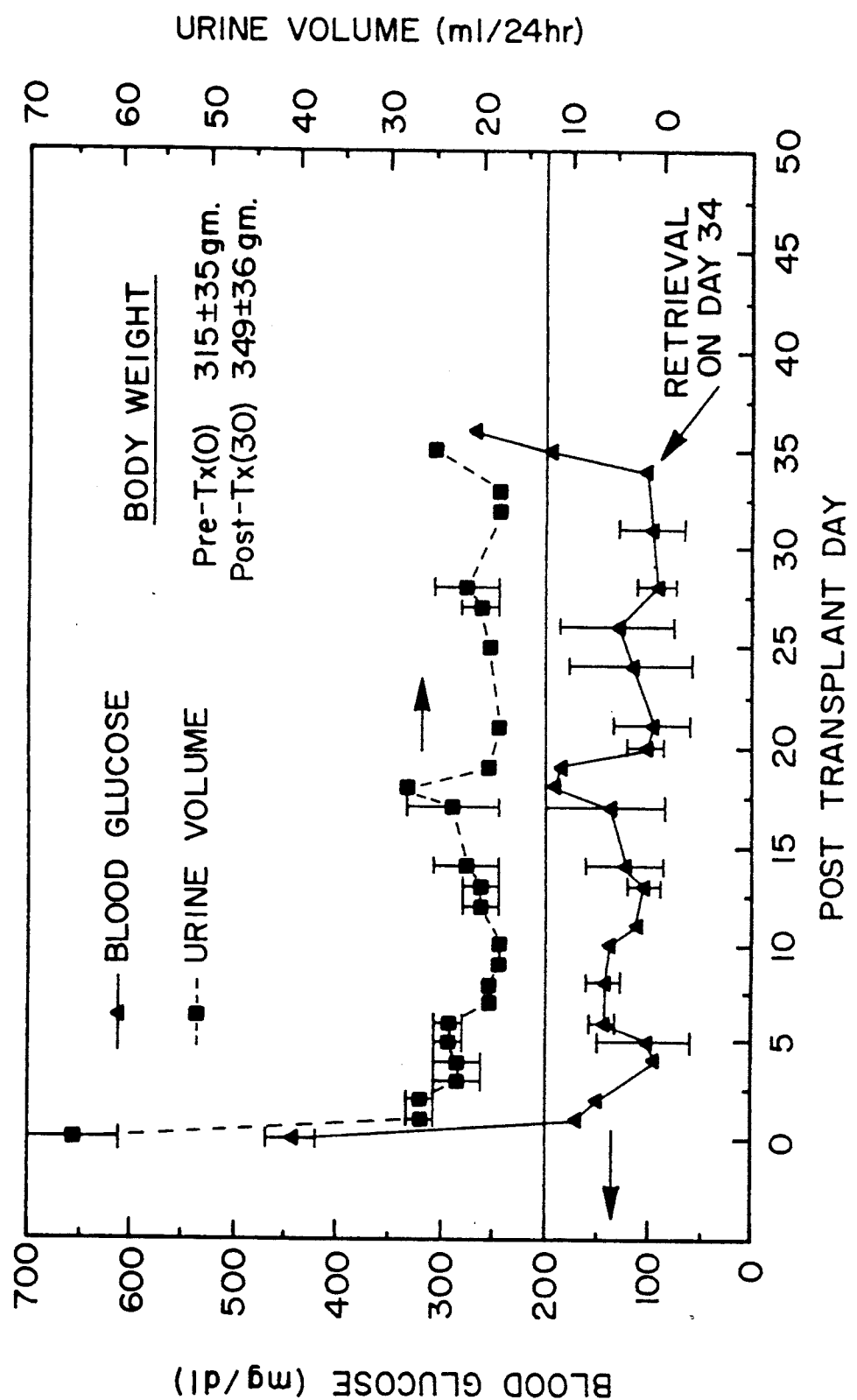
FIG. 5 is a graph of the effects on blood glucose, urine volume and body weight of dog to rat xenotransplanted islets in AP 10K microcapsules of the present invention.

FIG. 5 shows the blood glucose, urine volume and body weights of the rats receiving microencapsulated islets (AP 10 k solutions). 10,000 canine islets were transplanted into the peritoneal cavities of these rats. The blood glucose shows an immediate drop to normal levels Normoglycemia is maintained for 34 days at which time these implants are retrieved (although they are functioning normally) for purposes of assessing the state of the implant. Immediately after retrieval the blood glucose and urine volumes are seen to raise back towards diabetic levels. The body weights of these rats were seen to increase at a steady rate of approximately a gram per day during the period of the transplant which is typical in a healthy rat.

Figure 6:
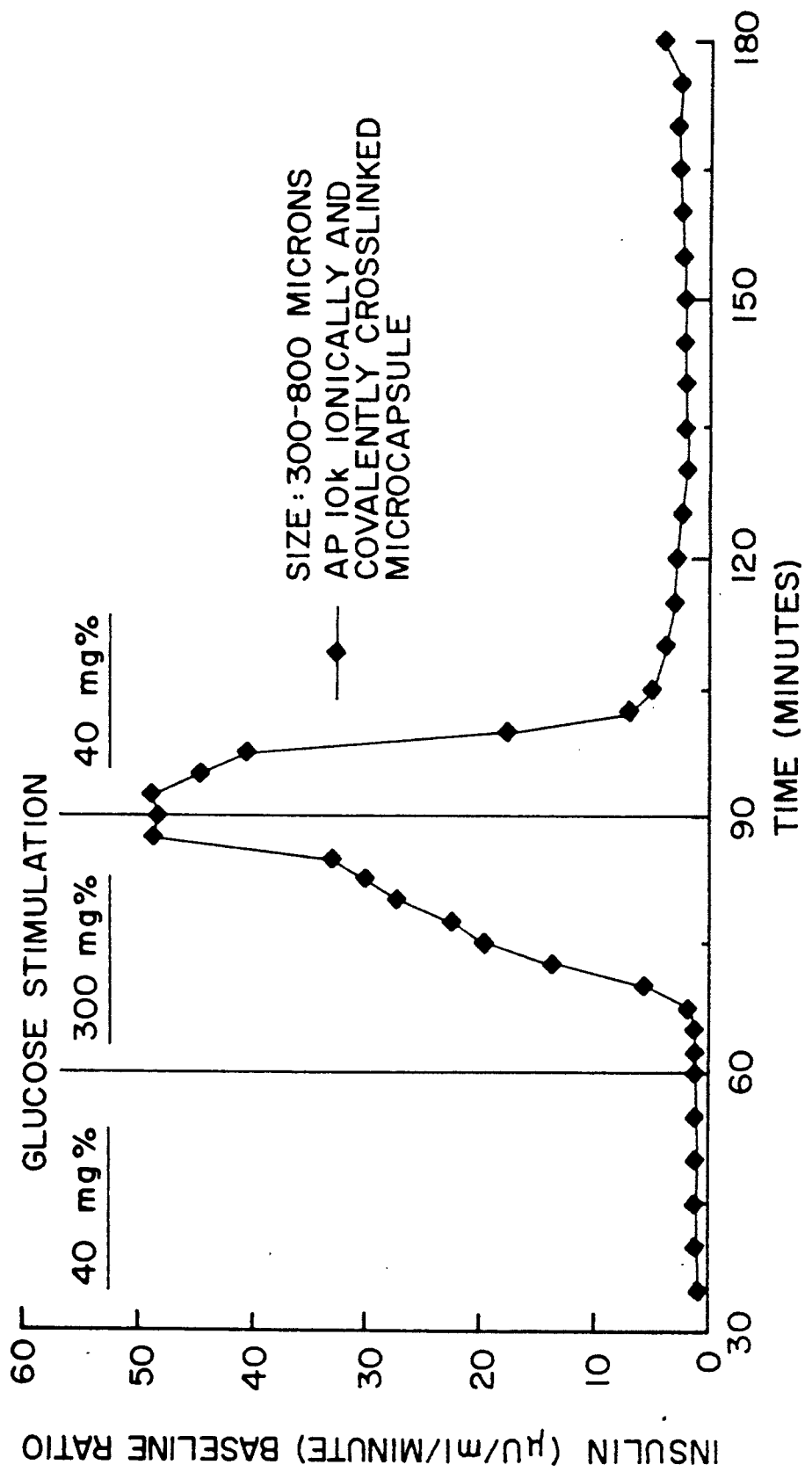
FIG. 6 is a perifusion graph of retrieved, dog to rat xenotransplanted islets in AP 10K microcapsules of the present invention.

The implanted microcapsules were recovered at 34 days and the animals sacrificed. The recovered microcapsules were cultured in vitro, observed for tissue reaction to the material, subject to viability staining, static glucose stimulation (SGS), and perifusion for assessment of islet function. Most of the microcapsules were free from tissue overgrowth and staining of islets with dithizone (stain for insulin) showed the presence of insulin in more than 80% of the recovered islets. SGS gave stimulation ratios to be 1.0:50.8:10.9 indicating extremely healthy islets. The perifusion profile (FIG. 6) of these recovered islets showed a result that essentially matched the SGS in terms of stimulation ratios showing the characteristic profiles of insulin secretion that were observed in in vitro studies prior to implantation.

Figure 7:
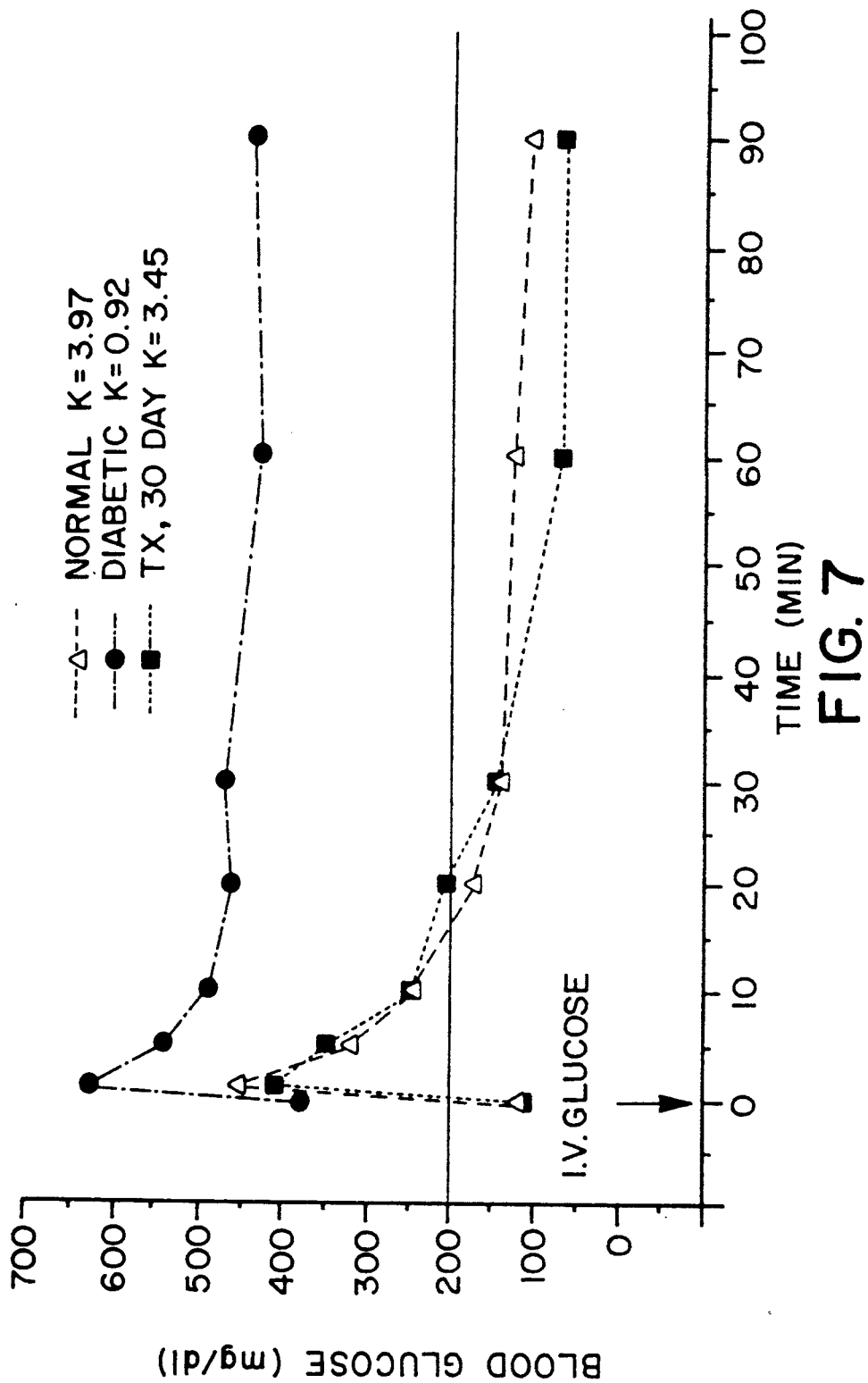
FIG. 7 is a graph of an intravenous glucose tolerance test on rats having implanted canine islets in AP microcapsules of the present invention.

An intravenous glucose tolerance test (IVGTT) was performed on the transplanted rats prior to retrieval of the implants to determine the kinetics of glucose clearance from the vascular system of these rats when challenged by an injection of glucose. The procedure involved the cannulation of the external jugular vein of these rats with a catheter under general anesthesia. The animals were then allowed to recover for a day or two. Glucose (500 mg/kg body weight) was administered through the catheter and blood was withdrawn periodically after the injection at 1, 5, 10, 20, 30, 60, and 90 minutes. Blood glucose was measured and plotted as a function of time to determine the rapidity of clearance from the vascular system of the rat. FIG. 7 shows these results. The rapidity of clearance is measured in terms of a K value which is computed by determining the slope of a line between the glucose values at 1 minute and 30 minutes plotted on a logarithmic scale. The higher the K value, the faster the clearance of glucose. For a normal rat, the K value is typically greater than 3.0 while for diabetic namilas it is significantly lower. The curves in FIG. 7 show the results for a normal rat, a diabetic rat, and a diabetic rat receiving a xenotransplant of canine islets in AP microcapsules, at 30 days after transplantation. The glucose clearance curve for the transplanted rat very closely approximates that of the normal rat indicating the success of the transplant and alleviation of diabetic symptoms.

Example 13

Figure 8:
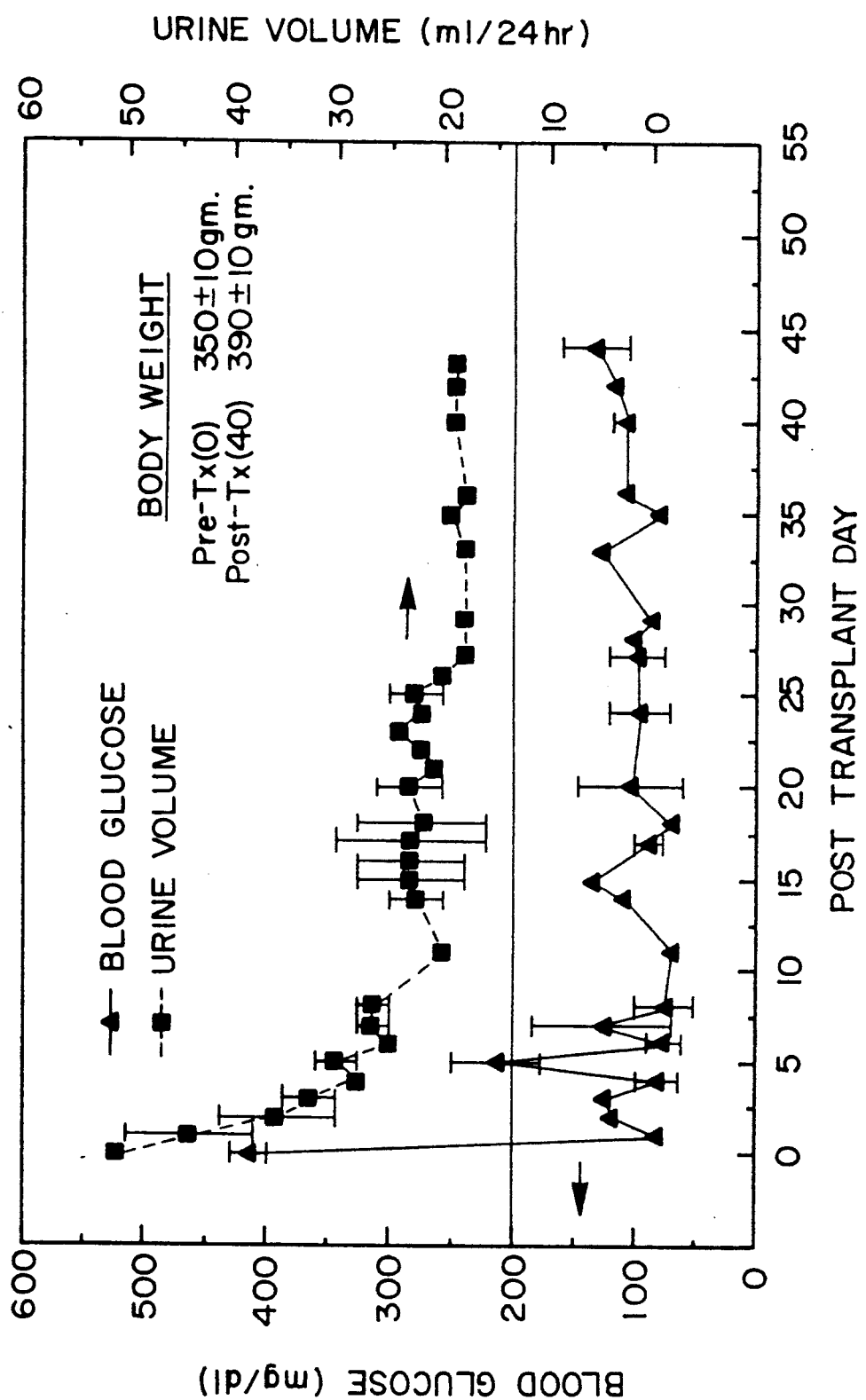
FIG. 8 is a graph showing the effects of a dog to rat xenotransplant of AP macrocapsules of the present invention containing canine islets in alginate/PLL microcapsules.

In Vivo Tests of Islet Function in a Xenotransplant Model with Conventional Alginate/PLL Microcapsules Further Encapsulated in AP Macrocapsules Canine islets encapsulated in conventional alginate/PLL microcapsules (MIC) were further encapsulated in AP 10 k macrocapsules by suspension of the MICs in the AP mixture and extrusion through a syringe to form droplets (5-7 mm diameter) into a calcium solution followed by photocrosslinking. These were transplanted into the peritoneal cavity of STZ induced diabetic rats and the blood glucose, urine volumes, and body weights monitored over time. FIG. 8 shows the results of these transplants indicating a complete reversal of diabetes in these rats as determined by their normal blood glucose levels (<200 mg/dl), normal urine volumes (15-25 ml/24 hours), and increase in body weights by approximately a gram per day. The status of these implants was ongoing for more than 45 days at the time of this application, totally independent from exogenous insulin requirements.

We claim:

1. A crosslinked biocompatible material comprising:
   at least one ionically crosslinked component; and
   at least one covalently crosslinked component, wherein the ionically crosslinked component is selected from a polysaccharide, a polyanion, or a polycation.

2. The crosslinked biocompatible material of claim 1, wherein the ionically crosslinked component is alginate.

3. The crosslinked biocompatible material of claim 2, wherein the alginate is a high G block alginate having at least 60% α-L-guluronic acid.

4. The crosslinked biocompatible material of claim 3, wherein the alginate comprises at least 70% α-L-guluronic acid.

5. The crosslinked biocompatible material of claim 2, further comprising a biologic encapsulated by the material.

6. The crosslinked biocompatible material of claim 5, wherein the material is effective to provide immunoprotection for the biologic in a physiological environment.

7. The crosslinked biocompatible material of claim 6, wherein the material provides immunoprotection of the biologic when xenotransplanted.

8. The crosslinked biocompatible material of claim 5, wherein the biologic is a biologically active material or a diagnostic marker.

9. The crosslinked biocompatible material of claim 8, wherein the biologically active materials are living cells selected from islets of Langerhans, dopamine secreting cells, erythropoietin secreting cells, nerve growth factor secreting cells, hepatocytes, adrenaline/angiotensin secreting cells, parathyroid cells, or norepinephrine/metacephalin secreting cells.

10. The crosslinked biocompatible material of claim 8, wherein the biologically active material is a drug.

11. A crosslinked biocompatible material comprising:
at least one ionically crosslinked component; and
at least one covalently crosslinked component, wherein the covalently crosslinked component is derived from a polyalkylene oxide.

12. The crosslinked biocompatible material of claim 11, wherein the covalently crosslinked component is polyethylene glycol diacrylate.

13. The crosslinked biocompatible material of claim 11, further comprising a biologic encapsulated by the material.

14. The crosslinked biocompatible material of claim 13, wherein the material is effective to provide immunoprotection for the biologic in a physiological environment.

15. The crosslinked biocompatible material of claim 14, wherein the material provides immunoprotection of the biologic when xenotransplanted.

16. The crosslinked biocompatible material of claim 13, wherein the biologic is a biologically active material or a diagnostic marker.

17. The crosslinked biocompatible material of claim 16, wherein the biologically active materials are living cells selected from islets of Langerhans, dopamine secreting cells, erythropoietin secreting cells, nerve growth factor secreting cells, hepatocytes, adrenaline/angiotensin secreting cells, parathyroid cells, or norepinephrine/metacephalin secreting cells.

18. The crosslinked biocompatible material of claim 16, wherein the biologically active material is a drug.

19. A crosslinkable biocompatible mixture comprising:
at least one ionically crosslinkable component; and
at least one covalently crosslinkable component, wherein the ionically crosslinkable component is selected from a polysaccharide, a polyanion, or a polycation.

20. The crosslinkable biocompatible mixture of claim 19, wherein the ionically crosslinkable component is alginate.

21. The crosslinkable biocompatible mixture of claim 20, wherein the alginate is capable of ionically crosslinking by adding multivalent cations to the mixture.

22. The crosslinkable biocompatible mixture of claim 19, wherein the composition ratio between the ionically crosslinkable component and the covalently crosslinkable component is effective for the stable crosslinking of the mixture, whereby a gelled encapsulation material is formed.

23. The crosslinkable biocompatible mixture of claim 22, wherein the concentration and the molecular weight(s) of the covalently crosslinkable component are effective to provide immunoprotection to the encapsulated functional core once the mixture has been crosslinked.

24. The crosslinkable biocompatible mixture of claim 23, wherein the mixture has an osmolarity and pH compatible with living tissue or cells.

25. The crosslinkable biocompatible mixture of claim 24, wherein the osmolarity of the mixture is about 290 milliosmoles per kilogram and the pH is about 7.4.

26. The crosslinkable biocompatible mixture of claim 23, wherein the concentration and molecular weight(s) of the covalently crosslinkable component are effective for the controlled release of the biologic or components of the biologic once the mixture has been crosslinked.

27. A crosslinkable biocompatible mixture comprising:
at least one ionically crosslinkable component; and
at least one covalently crosslinkable component, wherein the covalently crosslinkable component is a polyalkylene oxide.

28. The crosslinkable biocompatible mixture of claim 27, wherein the polyalkylene oxide is capable of covalently crosslinking by free radical polymerization.

29. The crosslinkable biocompatible mixture of claim 27, wherein the polyalkylene oxide is polyethylene glycol diacrylate.

30. The crosslinkable biocompatible mixture of claim 27, wherein the composition ratio between the ionically crosslinkable component and the covalently crosslinkable component is effective for the stable crosslinking of the mixture, whereby a gelled encapsulation material is formed.

31. The crosslinkable biocompatible mixture of claim 30, wherein the concentration and the molecular weight(s) of the covalently crosslinkable component are effective to provide immunoprotection to the encapsulated functional core once the mixture has been crosslinked.

32. The crosslinkable biocompatible mixture of claim 31, wherein the mixture has an osmolarity and pH compatible with living tissue or cells.

33. The crosslinkable biocompatible mixture of claim 32, wherein the osmolarity of the mixture is about 290 milliosmoles per kilogram and the pH is about 7.4.

34. The crosslinkable biocompatible mixture of claim 31, wherein the concentration and molecular weight(s) of the covalently crosslinkable component are effective for the controlled release of the biologic or components of the biologic once the mixture has been crosslinked.

35. A retrievable implantation material, comprising:
a crosslinked biocompatible macrocapsule comprising at least one ionically crosslinked component, and at least one covalently crosslinked component, whereby said macrocapsule, encapsulates a microcapsule(s) or a biologic.

36. The retrievable implantation material of claim 35, wherein the macrocapsule provides immunoprotection to the encapsulated microcapsule(s) or biologic when xenotransplanted.

* * * * *

(12) REEXAMINATION CERTIFICATE (4728th)
United States Patent
Desai et al.

(10) Number: US 5,334,640 C1
(45) Certificate Issued: Feb. 4, 2003

(54) IONICALLY COVALENTLY CROSSINKED AND CROSSLINKABLE BIOCOMPATIBLE ENCAPSULATION COMPOSITIONS AND METHODS

(75) Inventors: Neil P. Desai, Los Angeles, CA (US); Patrick Soon-Shiong, Los Angeles, CA (US); Paul A. Sandford, Los Angeles, CA (US); Roswitha E. Heintz, Los Angeles, CA (US)

(73) Assignee: Vivorx, Inc., Santa Monica, CA (US)

Reexamination Request:
No. 90/005,566, Nov. 18, 1999

Reexamination Certificate for:
Patent No.: 5,334,640
Issued: Aug. 2, 1994
Appl. No.: 07/866,038
Filed: Apr. 8, 1992

(51) Int. Cl.$^7$ .............. C08K 5/15; C08L 5/00; A61K 9/14; C12N 11/02
(52) U.S. Cl. .............. 524/56; 524/54; 524/28; 424/488; 424/499; 435/177; 435/178
(58) Field of Search ............................... 524/56

(56) References Cited

U.S. PATENT DOCUMENTS

| | | | |
|---|---|---|---|
| 4,791,061 A | 12/1988 | Sumino et al. | |
| 4,824,916 A | 4/1989 | Kershner et al. | |
| 5,041,292 A | 8/1991 | Feijen | |
| 5,268,286 A | 12/1993 | Kobayashi et al. | |
| 5,459,054 A | 10/1995 | Shjak-Braek et al. | |

FOREIGN PATENT DOCUMENTS

| | | | |
|---|---|---|---|
| GB | 2 237 574 A | 5/1991 | |

*Primary Examiner*—Paul R. Michl

(57) ABSTRACT

Crosslinked biocompatible compositions comprising an ionically crosslinked component and a covalently crosslinked component for encapsulating biologics are disclosed. In accordance with the present invention, also disclosed are crosslinkable biocompatible mixtures comprising an ionically crosslinkable component and a covalently crosslinkable component. Methods for encapsulating biologics with the crosslinked and crosslinkable biocompatible compositions are provided. Also, retrievable macrocapsules for encapsulating microcapsules or biologics are disclosed.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–36 are cancelled.

New claims 37–62 are added and determined to be patentable.

*37. A crosslinked biocompatible material comprising at least one covalently crosslinked component; and at least one ionically crosslinked component, wherein the covalently crosslinked component is a photopolymerized derivative of polyethylene glycol, and wherein the ionically crosslinked component is a polysaccharide, a polyanion, or a polycation.*

*38. The crosslinked biocompatible material of claim 37, wherein the covalently crosslinked component is polyethylene glycol diacrylate.*

*39. The crosslinked biocompatible material of claim 37, wherein the ionically crosslinked component is alginate.*

*40. The crosslinked biocompatible material of claim 39, wherein the alginate is capable of ionically crosslinking upon addition thereto of multivalent cations.*

*41. The crosslinked biocompatible material of claim 39, wherein the alginate is a high G block alginate having at least 60% α-L-guluronic acid.*

*42. The crosslinked biocompatible material of claim 39, wherein the alginate comprises at least 70% α-L-guluronic acid.*

*43. The crosslinked biocompatible material of claim 38, further comprising a biologic encapsulated by the material.*

*44. The crosslinked biocompatible material of claim 43, wherein the material is effective to provide immunoprotection for the biologic in a physiological environment.*

*45. The crosslinked biocompatible material of claim 43, wherein the material provides immunoprotection of the biologic when xenotransplanted.*

*46. The crosslinked biocompatible material of claim 43, wherein the biologic is a biologically active material or a diagnostic marker.*

*47. The crosslinked biocompatible material of claim 46, wherein the biologically active material is a drug.*

*48. A crosslinked biocompatible material comprising at least one covalently crosslinked component; and at least one ionically crosslinked component, wherein the ionically crosslinked component is a polysaccharide, a polyanion, or a polycation, and wherein the covalently crosslinked component comprises polymerized polyethylene glycol (PEG), said polymerized PEG having been formed from PEG monomers with a molecular weight of about 10,000.*

*49. A crosslinked biocompatible material comprising at least one covalently crosslinked component; and at least one ionically crosslinked component, wherein the covalently crosslinked component comprises polyethylene glycol monomer, and wherein the ratio of ionically crosslinked component to covalently crosslinked component is in the range of about 1:3.0 to 1:7.5.*

*50. A crosslinkable biocompatible material comprising a mixture of at least one covalently crosslinkable component; at least one ionically crosslinkable component, and a photoinitiator, wherein the covalently crosslinkable component comprises polyethylene glycol monomer, and wherein the ionically crosslinkable component is a polysaccharide, a polyanion, or a polycation.*

*51. The crosslinkable biocompatible mixture of claim 50, wherein the composition ratio between the ionically crosslinkable component and the covalently crosslinkable component is effective for the stable crosslinking of the mixture, whereby a gelled encapsulation material is formed.*

*52. The crosslinkable biocompatible mixture of claim 50, wherein the ratio of ionically crosslinked component to covalently crosslinked component is in the range of about 1:3.0 to 1:7.5.*

*53. The crosslinkable biocompatible mixture of claim 50, wherein the mixture has an osmolarity and pH compatible with living tissue or cells.*

*54. The crosslinkable biocompatible mixture of claim 53, wherein the osmolarity of the mixture is about 290 milliosmoles per kilogram and the pH is about 7.4.*

*55. The crosslinkable biocompatible mixture of claim 50, wherein the concentration and the molecular weight(s) of the covalently crosslinkable component are effective to provide immunoprotection to the encapsulated functional core once the mixture has been crosslinked.*

*56. The crosslinkable biocompatible mixture of claim 55, wherein the concentration and molecular weight(s) of the covalently crosslinkable component are effective for the controlled release of the biologic or components of the biologic once the mixture has been crosslinked.*

*57. A crosslinkable biocompatible material comprising at least one covalently crosslinkable component; and at least one ionically crosslinkable component, wherein the ionically crosslinkable component is a polysaccharide, a polyanion, or a polycation, and wherein the covalently crosslinkable component comprises polyethylene glycol monomer having a molecular weight of about 10,000.*

*58. A crosslinkable biocompatible material comprising at least one covalently crosslinkable component; and at least one ionically crosslinkable component, wherein the covalently crosslinked component comprises polyethylene glycol monomer, and wherein the ratio of ionically crosslinkable component to covalently crosslinkable component is in the range of about 1:3.0 to 1:7.5.*

59. A retrievable implantation material, comprising:

a crosslinked biocompatible macrocapsule comprising at least one ionically crosslinked component, and at least one covalently photocrosslinked component, whereby said macrocapsule encapsulates a microcapsule(s) or a biologic.

60. The retreivable implantation material of claim 59, wherein the macrocapsule provides immunoprotection to the encapsulated microcapsule(s) or biologic when xenotransplanted.

61. A biologically active material encapsulated in a crosslinked biocompatible material, wherein said crosslinked biocompatible material comprises:

at least one ionically crosslinked component; and at least one covalently crosslinked component, wherein the ionically crosslinked component is an alginate, and wherein the biologically active materials are living cells selected from islets of Langerhans, dopamine secreting cells, erythropoietin secreting cells, nerve growth factor secreting cells, hepatocytes, adrenaline/angiotensin secreting cells, parathyroid cells, or norepinephrine/metacephalin secreting cells.

62. A biologic encapsulated in a crosslinked biocompatible material, wherein said crosslinked biocompatible material comprises:

at least one ionically crosslinked component; and at least one covalently crosslinked component, wherein the covalently crosslinked component is dervied from a polyalkylene oxide, and wherein the biologic is a diagnostic marker, or a biologically active material selected from living cells selected from islets of Langerhans, dopamine secreting cells, erythropoietin secreting cells, nerve growth factor secreting cells, hepatocytes, adrenaline/angiotensin secreting cells, parathyroid cells, or norepinephrine/metacephalin secreting cells.

* * * * *